(12) United States Patent
Mamenta

(10) Patent No.: US 10,677,807 B2
(45) Date of Patent: Jun. 9, 2020

(54) SYSTEM AND METHOD FOR SAMPLE COLLECTION, TRANSPORT AND ANALYSIS

(71) Applicant: Edward L Mamenta, Natick, MA (US)

(72) Inventor: Edward L Mamenta, Natick, MA (US)

( * ) Notice: Subject to any disclaimer, the term of this patent is extended or adjusted under 35 U.S.C. 154(b) by 714 days.

(21) Appl. No.: 15/290,926

(22) Filed: Oct. 11, 2016

(65) Prior Publication Data

US 2017/0102399 A1 Apr. 13, 2017

Related U.S. Application Data

(60) Provisional application No. 62/284,777, filed on Oct. 9, 2015.

(51) Int. Cl.
| | |
|---|---|
| *G01N 33/80* | (2006.01) |
| *G01N 33/49* | (2006.01) |
| *G01N 1/40* | (2006.01) |
| *G01N 21/84* | (2006.01) |
| *A61B 5/15* | (2006.01) |
| *G01N 1/00* | (2006.01) |
| *G01N 21/77* | (2006.01) |
| *A61B 10/00* | (2006.01) |
| *B01L 3/00* | (2006.01) |

(52) U.S. Cl.
CPC ....... *G01N 33/80* (2013.01); *A61B 5/150022* (2013.01); *A61B 5/150358* (2013.01); *G01N 1/405* (2013.01); *G01N 21/8483* (2013.01); *G01N 33/491* (2013.01); *A61B 10/007* (2013.01); *A61B 10/0045* (2013.01); *A61B 10/0051* (2013.01); *B01L 3/5023* (2013.01); *B01L 2300/069* (2013.01); *B01L 2300/0825* (2013.01); *B01L 2300/126* (2013.01); *G01N 2001/005* (2013.01); *G01N 2021/7766* (2013.01)

(58) Field of Classification Search
CPC ........................................................ G01N 33/80
USPC .............................................................. 702/19
See application file for complete search history.

(56) References Cited

U.S. PATENT DOCUMENTS

2013/0011042 A1 * 1/2013 Satish ...................... G06K 9/00
382/134

* cited by examiner

*Primary Examiner* — Jerry Lin
(74) *Attorney, Agent, or Firm* — Daniel N. Smith

(57) ABSTRACT

A system and method for collecting, transporting, and analyzing dried bodily fluid samples using a sample collection device incorporating extraction markers, an imaging device to take images of dried samples on the collection device, and a computing device to analyze data points from the images so as to measure various properties of the collected sample such as the volume of blood initially collected, and the portion of that volume containing plasma and erythrocytes.

16 Claims, 29 Drawing Sheets

Fig. 15
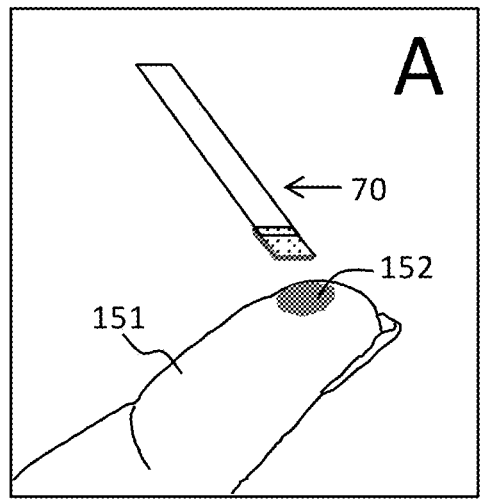
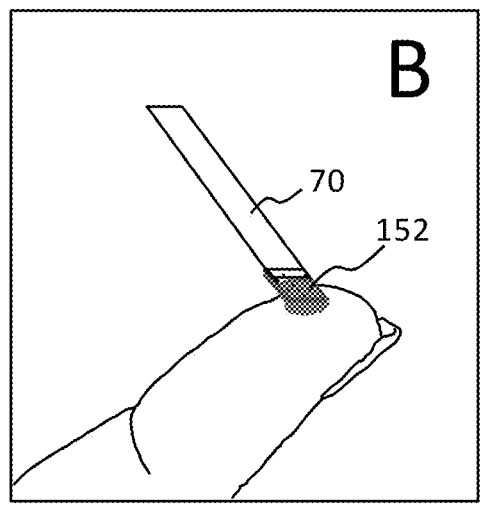
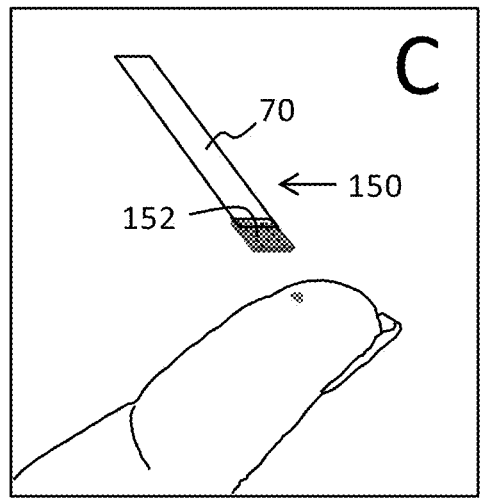

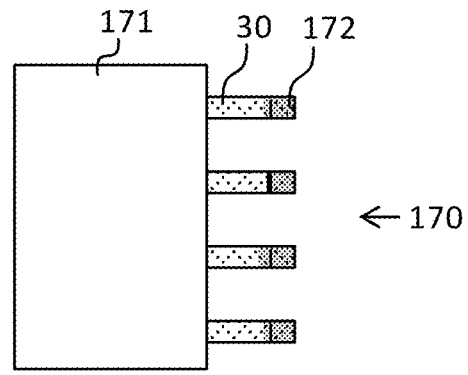
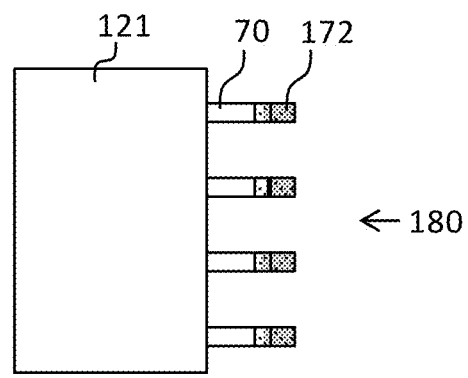
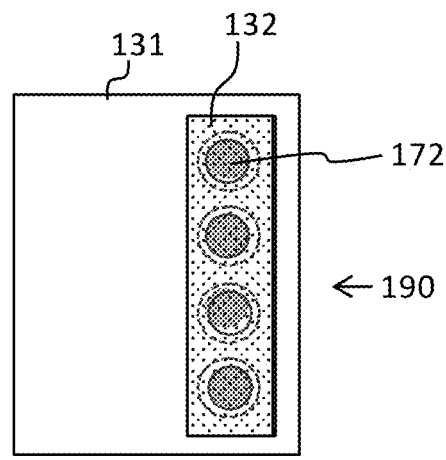

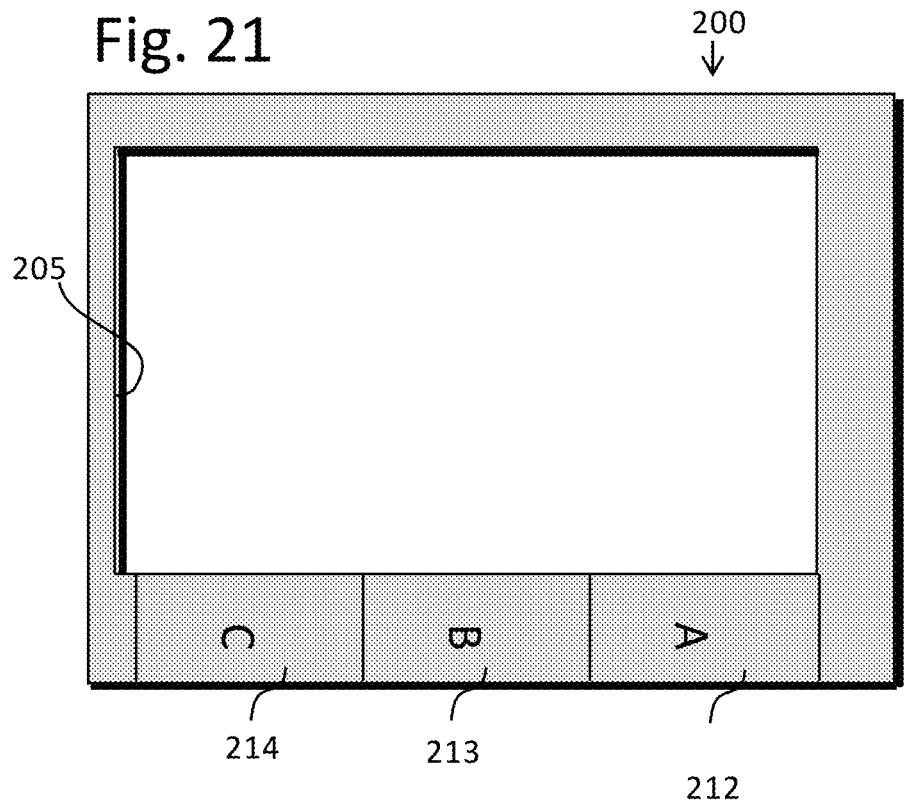
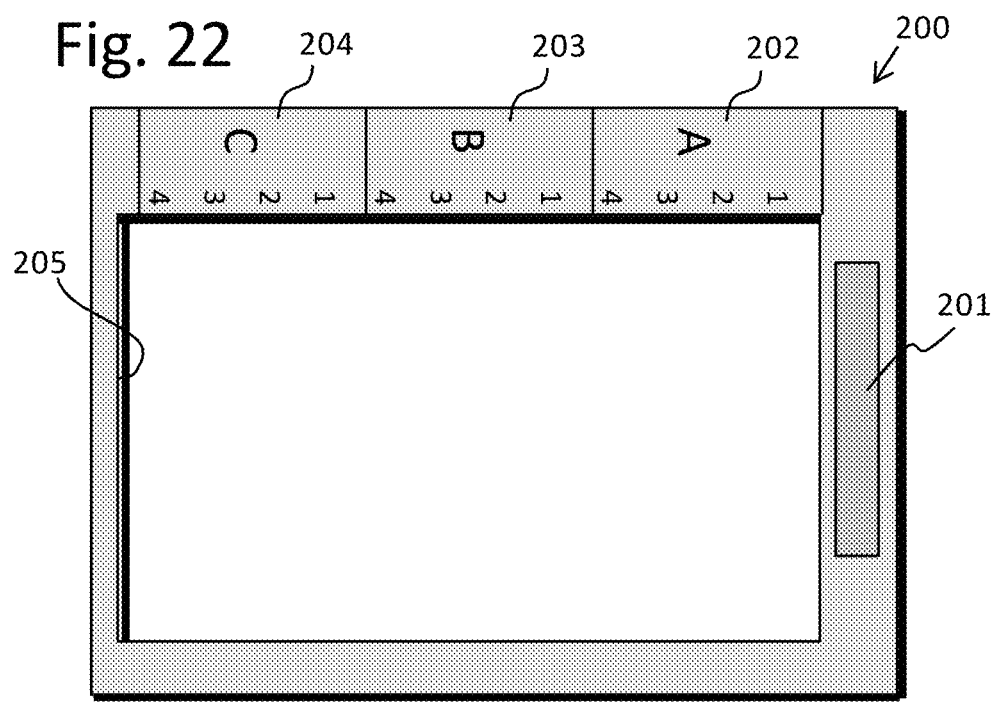

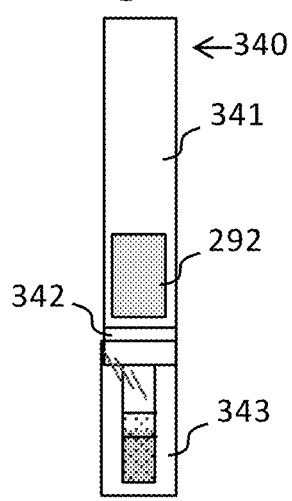
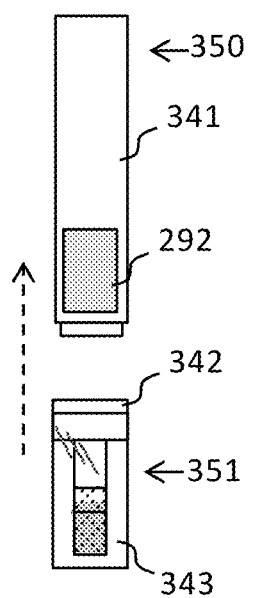
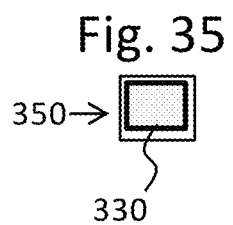

SYSTEM AND METHOD FOR SAMPLE COLLECTION, TRANSPORT AND ANALYSIS

CROSS REFERENCE TO RELATED APPLICATION

This application claims the benefit of U.S. Provisional Patent Application No. 62/284,777, filed on Oct. 9, 2015; the contents of which are incorporated herein by reference.

FIELD OF THE INVENTION

The present invention relates to a system and method for collecting, transporting and analyzing blood and other samples.

BACKGROUND OF THE INVENTION

Clinical laboratory tests provide physicians and other healthcare workers with critical information to aid in the diagnosis and prognosis of medical conditions. The importance of clinical laboratory tests is underscored by the fact that over 70% of healthcare decisions are based upon these tests. Many, if not most, clinical laboratory tests rely on safe, quick, reliable, and repeatable collection, transportation, and analysis of blood samples.

Typically, blood samples are collected by trained phlebotomists who draw blood into a tube connected to a needle that is inserted into a donor's vein. Many individuals are fearful or uncomfortable with this method of blood collection. Also, the need for a trained phlebotomist to collect the sample limits the number of locations where samples can be collected, often resulting in much inconvenience for the donor, and adds labor costs to the overall collection process.

If the sample is intended for analysis at a distant laboratory, various protocols must be observed in preparing and sending a shipment of the sample to ensure the integrity of the sample, identity of the sample, and safety of individuals who may come into contact with the shipment. Samples are usually placed in a refrigerated shipping container and transported to laboratories through an expedited shipping method. These steps add considerable costs to the testing process. The stability of certain target analytes during the transport process is also of concern.

Given the expenses and analytical variables associated with the conventional process of collecting, transporting, and analyzing blood samples, along with the drawbacks this process imposes on sample donors, alternative approaches have been actively pursued. One such approach focuses on expanding the use of dried blood spot (DBS) methods. With DBS, small blood samples, usually obtained from a finger or heel prick, are spotted and dried onto specialized filter paper. The dried samples can then be shipped to a laboratory through the mail without the need for refrigeration.

Although DBS sampling provides certain advantages over conventional syringe blood collections, the technology also has a number of drawbacks that severely limit its utility.

Once a DBS sample has reached the laboratory, analytes must be recovered through an extraction process which involves punching out an area of sample-containing filter paper for analysis. Typically, a circular disc with a 3-6 mm diameter is punched out with an instrument that must come into direct contact with the sample-containing filter, potentially contaminating the instrument, and requiring that the instrument be decontaminated between sample punches. This procedure also requires considerably more blood to be collected than is actually used in the analysis.

Another problem with the DBS method is its inability to provide a precisely defined volume of sample to assay, due to the inherent variability of sample hematocrit values (the percentage of blood volume comprised of red blood cells). This problem, sometimes referred to as "hematocrit bias", occurs because red blood cells affect sample viscosity (viscosity increases in proportion to red blood cell concentration) and viscosity in turn affects the amount of area covered by a blood sample on a piece of collection paper (for a given volume of blood, less viscous samples will spread out over a larger area of collection paper). Standard laboratory procedures usually calculate volume based on the average hematocrit level for a given population, resulting in a considerable underestimation or overestimation for those samples that have hematocrit values considerably different from the mean. This presumptive step can proportionately bias the value of the test result, in some cases resulting in miscalculations greater than 20%.

Another problem with the DBS method is the tendency for certain analytes in a sample to become heterogeneously distributed through the paper matrix due to chromatographic effects of the paper. This can lead to inaccurate results as areas of the paper collected for sampling may have variably lower or higher concentrations of the target analyte.

Still another problem with the DBS method has to do with variability in analyte recovery during the extraction process. Conventional DBS methods provide no practical approach for monitoring the efficiency of analyte recovery which can lead to significant underestimation of analyte concentration.

While the DBS method does not require a phlebotomist to collect the sample, there are critical steps in the procedure that, if not performed properly, can lead to erroneous test results. For example, touching the filter paper or applying too small a volume can lead to variations in sample volume per unit area. While proper spotting technique may mitigate this variability, the technique itself is often difficult for donors to appropriately master. The donor must create a hanging drop that is sufficiently large, but not so large that it accidentally drips from the finger (which can cause splattering and contamination). The drop must then be applied to the filter paper in such a way that inadvertently causes the finger to obscure from view the contact point between the blood sample and paper, contributing to the possibility that the donor will accidentally touch the paper or apply an insufficient amount of sample.

Thus, there remains a compelling need to develop test systems and methods that can incorporate dried blood samples in a way that solves the problems that exist with all current approaches.

The present invention provides a simple and easy-to-use means for collecting and drying a sample of blood, transporting the dried blood to a laboratory, and analyzing the dried blood sample with a level of accuracy, consistency, and reliability not achievable with current approaches. In particular, the present invention provides a collection procedure considerably more user-friendly than the standard DBS procedure and resolves the problematic DBS issues regarding hematocrit bias, chromatographic effects, and variable extraction recoveries.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The present invention provides a system and method for collecting, transporting and analyzing blood samples or other fluid samples. The system comprises an assay/collection device incorporating extraction markers, an imaging device operatively connected to the assay/collection device, and a computing device operatively connected to the imaging device, wherein the computing device comprises an executable software program capable of analyzing data points from the imaging device so as to measure various properties of the collected sample, such as the volume of blood initially collected on the assay/collection device, and the portion of that volume comprising plasma and erythrocytes. The software program also performs further calculations by incorporating data points obtained from additional devices or procedures. The method of the invention comprises collecting a volume of blood sample with the assay/collection device and transporting the sample-containing device to a second location as a dried sample, eliminating the need for conditions or expenses associated with the transport of liquid blood sample. For example, the device may be transported to a second location without the need for refrigeration or expedited delivery times. The method of the invention further comprises collecting one or more digital images of the sample-containing assay/collection device with the imaging device. After a sufficient number of images have been collected, the sample contained within the collection device is subjected to an extraction process that converts the dried sample to a fluid sample, with the fluid sample containing the extraction markers in a concentration indicative of the extraction efficiency. The fluid sample is then subjected to one or more laboratory analyses that measure both the analytes of interest within the sample and the extraction markers, and the resulting data is combined with the digital image data to derive an assay result.

The assay/collection device allows for the rapid, simple collection of a volume of blood. The device comprises a sample region made of absorbent wicking material capable of fluid sample collection by capillary action. The sample region may be comprised of any suitable material including, but not limited to, Whatman 903 filter paper, Whatman DMPK filter paper or Whatman FTA filter paper Ahlstrom Grade 226 filter paper and/or Munktell TFN filter paper.

In a preferred embodiment, the absorbent material is configured into a strip with some, or all, of the strip comprising the absorbent sample region, thereby generating a strip-based assay/collection device. In some embodiments, the absorbent sample region is connected to a non-absorbent support. The sample region is connected to the support through any suitable means including, but not limited to, an adhesive. In a preferred embodiment, the support is comprised of a non-absorbent plastic. The device may also contain backings, labels or tags to identify the sample, such as a label with an alpha numeric code or barcode, and a location to write or otherwise supply information related to the sample, such as the name of the sample donor. A blood sample may be collected onto the device by placing the sample region into contact with the sample and allowing the sample to migrate onto the sample region by capillary action. A marking, such as a fill line, may be incorporated onto, or in the vicinity of, the sample region indicating that sufficient sample has been collected.

In a preferred embodiment, the sample region contains extraction markers dried onto it, suitable for determining the efficiency of target analyte extractions. Extraction markers may be selected from a list of analytes that would not be expected to exist in the sample.

Examples of extraction markers include deuterium-labeled compounds and amplifiable nucleic acid targets.

In another preferred embodiment, the absorbent sample region is configured into a card rather than a strip. In the card configuration of the collection/assay device, a blood sample may be applied as a drop and allowed to migrate radially through the absorbent sample region, thereby generating a blood spot. A marking, such as a circle, may be incorporated onto the sample region indicating the target location where the blood sample should be applied and the approximate amount of sample to be applied (by, for example, instructing the user to fill most or all of the circle). In a preferred embodiment, extraction markers are dried onto the area contained within the marked circle. In some embodiments, the collection device may contain a perforation encircling the marked circle allowing for the sample-containing portion to be removed from the device without the need for cutting equipment.

In a preferred embodiment, the sample region contains extraction markers dried onto it, suitable for determining the efficiency of target analyte extractions. Extraction markers may be selected from a list of analytes that would not be expected to exist in the sample. Examples of extraction markers include deuterium-labeled compounds and amplifiable nucleic acid targets.

The invention further comprises an imaging device upon which the sample-containing collection device may be placed for imaging and analysis. The device comprises an imaging instrument (such as a digital scanner containing a camera and a light source), operatively connected to a computing device (such as a tablet, laptop, or desktop computer) wherein the computing device comprises an executable software program capable of collecting and analyzing data from the imaging device. In a preferred embodiment, the imaging device is used to collect one or more digital images of a sample-containing sample region which may then be received by the computing device (as a set of data points) for subsequent analysis. The imaging device may also be used to collect one or more images of an information-containing label or tag associated with the collection device. In a preferred embodiment, the imaging device is used to measure area and color value units associated with the dried sample, and use these measurements to determine the hematocrit level and volume of a blood sample originally collected (i.e. prior to drying) by the device. Put another way, these measurements can be used to determine the volume of a whole blood sample originally collected by the device, as well as the volume of plasma contained within this whole blood sample and the volume of red blood cells contained within this whole blood sample.

The invention further comprises a means for converting a dried sample (contained on the assay/collection device) into a liquid extract suitable for one or more assays. In a preferred embodiment, the sample containing portion of the device is placed into a suitable container (tube, microwell, vial etc.) and a defined volume of extraction fluid is added to the container so that the sample-containing portion of the device becomes submerged into the extraction fluid. In some embodiments, the sample containing portion of the collection device is first separated from the device and placed into the container. The container is then subjected to a physical agitation process (e.g. shaking, vortexing, sonicating) allowing for the components of the dried sample to become dissolved into the extraction fluid. In a preferred embodiment, the container is placed into a sonicator bath and subjected to sonication. After a sufficient period of time undergoing sonication, a sample extract is generated. In some embodiments, the sample extract is further processed, such as by filtration, centrifugation and/or solid-phase extraction, to remove insoluble matter, concentrate target analytes and/or otherwise render the extract more suitable for analysis.

The invention further comprises a method for subjecting the sample extract to one or more assay procedures including, but not limited to, procedures incorporating chromatography, mass spectrometry, immunoassays, chemical assays, biochemical assays, biological assays, and nucleic acid amplification assays. In some embodiments, the sample extract is subjected to optical density or colorimetric analysis with a photo-optic instrument (such as a spectrophotometer or microplate reader) to provide information related to the efficiency of the extraction process. Following the completion of the imaging and assay steps, a set of imaging and assay data points are generated.

The invention further comprises a computing device, wherein the device comprises an executable software program capable of analyzing data points from the imaging device so as to measure various properties of the collected sample. The software program may also be capable of performing further calculations by incorporating data points, such as assay data points, obtained from additional devices or procedures. In a preferred embodiment, the computing device receives data points from the imaging device and uses these data points to calculate the total volume of blood initially collected on the collection device (prior to a drying step) and the percentage of the total volume attributable to red blood cells in the sample (i.e. sample hematocrit). The computing device may also receive certain assay data points to calculate the extraction recovery of a target analyte (based on the extraction recovery of one or more extraction markers contained on the assay/collection device). In some embodiments, the computing device comprises (or is linked to) a database containing information related to the erythrocyte partitioning coefficient of target analytes, and uses this database to calculate the concentration of target analytes contained within the plasma or serum portion of the blood sample.

The subject invention discloses a method for determining the volume of a blood sample, the fraction of the blood sample volume composed of plasma, and the fraction of the blood sample volume composed of red blood cells, the method comprising: a) collecting the blood sample on an assay/collection device, the assay/collection device comprising an absorbent material capable of collecting the blood sample by capillary action and producing an observable colorimetric pattern from the blood sample; b) drying the blood sample on the assay/collection device; c) recording the colorimetric pattern on the assay/collection device as a first set of data points with an imaging device; and d) receiving and analyzing the first set of data points from the imaging device with a computing device operatively connected to the imaging device using an executable software program to derive: i) the volume of the blood sample collected by the assay/collection device, ii) the fraction of the blood sample volume composed of plasma; and iii) the fraction of the blood sample volume composed of red blood cells.

The subject invention also discloses a method for determining the concentration of a target analyte in a blood sample, the method comprising: a) collecting the blood sample on an assay/collection device, the collection device comprising an absorbent material capable of collecting the blood sample by capillary action and producing an observable colorimetric pattern from the blood sample; b) drying the blood sample on the assay/collection device; c) recording the colorimetric pattern on the collection device as a first set of data points with an imaging device; d) receiving and analyzing the first set of data points from the imaging device with a computing device operatively connected to the imaging device using an executable software program to derive: i) the volume of the blood sample collected by the assay/collection device, ii) the fraction of the blood sample volume composed of plasma; iii) the fraction of the blood sample volume comprising red blood cells; e) extracting the dried blood sample from the assay/collection device with an extraction solution to produce a fluid sample extract; f) determining the mass of the target analyte in the fluid sample extract with an assay; and g) combining the target analyte mass determination in step f) with the blood sample volume determination in step d) to derive the concentration of the target analyte in the blood sample.

The subject invention further discloses a method for determining the concentration of a target analyte in a plasma portion of a blood sample, the method comprising: a) collecting the blood sample on an assay/collection device, the assay/collection device comprising an absorbent material capable of collecting the blood sample by capillary action and producing an observable colorimetric pattern from the blood sample; b) drying the blood sample on the assay/collection device; c) recording the colorimetric pattern on the assay/collection device as a first set of data points with an imaging device; d) receiving and analyzing the first set of data points from the imaging device with a computing device operatively connected to the imaging device using an executable software program to derive: i) the volume of the blood sample collected by the assay/collection device, ii) the fraction of the blood sample volume composed of plasma; iii) the fraction of the blood sample volume comprising red blood cells; e) extracting the dried blood sample from the assay/collection device with an extraction solution to produce a fluid sample extract; f) determining the mass of the target analyte in the fluid sample extract with an assay; g) combining the target analyte mass determination in step f) with the blood sample volume determination in step d) to derive the concentration of the target analyte in the blood sample; h) providing a red blood cell partitioning coefficient for the target analyte, and i) combining the mass of the target analyte, the fraction of the blood sample volume composed of plasma, the fraction of the blood sample volume comprising red blood cells, and the red blood cell partitioning coefficient to derive the concentration of the target analyte in the plasma portion of the blood sample.

The subject invention discloses a method for determining the volume of a blood sample, the fraction of the blood sample volume composed of plasma, and the fraction of the blood sample volume composed of red blood cells, the method comprising: a) collecting the blood sample on an assay/collection device at a first location, the assay/collection device comprising an absorbent material capable of collecting the blood sample by capillary action and producing an observable colorimetric pattern from the blood sample; b) drying the blood sample on the assay/collection device; c) transporting the assay/collection device with the dried blood to a second location without cold storage or refrigeration; d) recording the colorimetric pattern on the assay/collection device as a first set of data points with an imaging device at the second location; and e) receiving and analyzing the first set of data points from the imaging device with a computing device operatively connected to the imaging device using an executable software program to derive: i) the volume of the blood sample collected by the assay/collection device, ii) the fraction of the blood sample volume composed of plasma; and iii) the fraction of the blood sample volume composed of red blood cells.

The subject invention also discloses a method for determining the concentration of a target analyte in a blood sample, the method comprising: a) collecting the blood sample on an collection device, the collection device comprising an absorbent material capable of assay/collecting the blood sample by capillary action and producing an observable colorimetric pattern from the blood sample; b) drying the blood sample on the assay/collection device; c) transporting the collection device with the dried blood to a second location without cold storage or refrigeration; d) recording the colorimetric pattern on the assay/collection device as a first set of data points with an imaging device at the second location; e) receiving and analyzing the first set of data points from the imaging device with a computing device operatively connected to the imaging device using an executable software program to derive: i) the volume of the blood sample collected by the assay/collection device, ii) the fraction of the blood sample volume composed of plasma; iii) the fraction of the blood sample volume comprising red blood cells; f) extracting the dried blood sample from the collective device with an extraction solution to produce a fluid sample extract; g) determining the mass of the target analyte in the fluid sample extract with an assay; and h) combining the target analyte mass determination in step g) with the blood sample volume determination in step e) to derive the concentration of the target analyte in the blood sample.

The subject invention further discloses a method for determining the concentration of a target analyte in a plasma portion of a blood sample, the method comprising: a) collecting the blood sample on an assay/collection device, the assay/collection device comprising an absorbent material capable of collecting the blood sample by capillary action and producing an observable colorimetric pattern from the blood sample; b) drying the blood sample on the assay/collection device; c) transporting the assay/collection device with the dried blood to a second location without cold storage or refrigeration; d) recording the colorimetric pattern on the assay/collection device as a first set of data points with an imaging device at the second location; e) receiving and analyzing the first set of data points from the imaging device with a computing device operatively connected to the imaging device using an executable software program to derive: i) the volume of the blood sample collected by the assay/collection device, ii) the fraction of the blood sample volume composed of plasma; iii) the fraction of the blood sample volume composed of red blood cells; f) extracting the dried blood sample from the assay/collection device with an extraction solution to produce a fluid sample extract; g) determining the mass of the target analyte in the fluid sample extract with an assay; h) combining the target analyte mass determination in step g) with the blood sample volume determination in step e) to derive the concentration of the target analyte in the blood sample; i) providing a red blood cell partitioning coefficient for the target analyte, and j) combining the mass of the target analyte, the fraction of the blood sample volume composed of plasma, the fraction of the blood sample volume composed of red blood cells, and the red blood cell partitioning coefficient to derive the concentration of the target analyte in the plasma portion of the blood sample.

A method for determining the volume of a blood sample, the fraction of the blood sample volume composed of plasma, and the fraction of the blood sample volume composed of red blood cells, the method comprising: a) collecting the blood sample on an assay/collection device, the assay/collection device comprising an absorbent material capable of collecting the blood sample as a drop that is allowed to migrate radially through the absorbent material, thereby generating a blood spot and producing an observable colorimetric pattern from the blood sample; b) drying the blood sample on the assay/collection device; c) recording the colorimetric pattern on the assay/collection device as a first set of data points with an imaging device; and d) receiving and analyzing the first set of data points from the imaging device with a computing device operatively connected to the imaging device using an executable software program to derive: i) the volume of the blood sample collected by the assay/collection device, ii) the fraction of the blood sample volume composed of plasma; and iii) the fraction of the blood sample volume composed of red blood cells.

A method for determining the volume of a blood sample, the fraction of the blood sample volume composed of plasma, and the fraction of the blood sample volume composed of red blood cells, the method comprising: a) collecting the blood sample on an assay/collection device, the assay/collection device comprising an absorbent material capable of collecting the blood sample as a drop that is allowed to migrate radially through the absorbent material, thereby generating a blood spot and producing an observable colorimetric pattern from the blood sample; b) drying the blood sample on the assay/collection device; c) transporting the assay/collection device from a first location to a second location without cold storage or refrigeration; d) recording the colorimetric pattern on the assay/collection device as a first set of data points with an imaging device at the second location; and e) receiving and analyzing the first set of data points from the imaging device with a computing device operatively connected to the imaging device using an executable software program to derive: i) the volume of the blood sample collected by the collection device, ii) the fraction of the blood sample volume composed of plasma; and iii) the fraction of the blood sample volume composed of red blood cells;

A method for determining the volume of a blood sample, the fraction of the blood sample volume composed of plasma, and the fraction of the blood sample volume composed of red blood cells, the method comprising: a) collecting the blood sample on an assay/collection device, the assay/collection device comprising an absorbent material capable of collecting the blood sample as a drop that is allowed to migrate radially through the absorbent material, thereby generating a blood spot and producing an observable colorimetric pattern from the blood sample; b) drying the blood sample on the assay/collection device; c) recording the colorimetric pattern on the assay/collection device as a first set of data points with an imaging device; and d) receiving and analyzing the first set of data points from the imaging device with a computing device operatively connected to the imaging device using an executable software program to derive: i) the volume of the blood sample collected by the assay/collection device, ii) the fraction of the blood sample volume composed of plasma; and iii) the fraction of the blood sample volume composed of red blood cells; e) extracting the dried blood sample from the assay/collective device with an extraction solution to produce a fluid sample extract; f) determining the mass of the target analyte in the fluid sample extract with an assay; and g) combining the target analyte mass determination in step f) with the blood sample volume determination in step d) to derive the concentration of the target analyte in the blood sample.

A method for determining the volume of a blood sample, the fraction of the blood sample volume composed of plasma, and the fraction of the blood sample volume composed of red blood cells, the method comprising: a) collecting the blood sample on an assay/collection device, the assay/collection device comprising an absorbent material capable of collecting the blood sample as a drop that is allowed to migrate radially through the absorbent material, thereby generating a blood spot and producing an observable colorimetric pattern from the blood sample; b) drying the blood sample on the assay/collection device;

c) transporting the assay/collection device from a first location to a second location without cold storage or refrigeration; d) recording the colorimetric pattern on the assay/collection device as a first set of data points with an imaging device at the second location; and e) receiving and analyzing the first set of data points from the imaging device with a computing device operatively connected to the imaging device using an executable software program to derive: i) the volume of the blood sample collected by the collection device, ii) the fraction of the blood sample volume composed of plasma; and iii) the fraction of the blood sample volume composed of red blood cells; f) extracting the dried blood sample from the assay/collective device with an extraction solution to produce a fluid sample extract; g) determining the mass of the target analyte in the fluid sample extract with an assay; and h) combining the target analyte mass determination in step g) with the blood sample volume determination in step e) to derive the concentration of the target analyte in the blood sample.

The subject invention discloses a system for determining the volume of a blood sample, comprising: a computing device comprising executable software; a data storage device; an imagine device; a blood sample assay/collection device comprising an absorbent material capable of collecting the blood sample by capillary action and producing an observable colorimetric pattern from the blood sample; a database of grayscale values and pixel counts corresponding to a plurality of colorimetric patterns produced by a plurality of dried blood sample volumes collected on an assay/collection device; wherein the blood sample is collected and dried on the assay/collection device, the colorimetric pattern of the dried blood sample is recorded as a set of data points with the imaging device; and further wherein the executable software program compares the colorimetric pattern of the dried blood sample with the database of grayscale values and pixel counts to derive the volume of the blood sample collected by the assay/collection device.

The subject invention discloses a system for determining the volume of a blood sample, comprising: a computing device comprising executable software; a data storage device; an imagine device; a blood sample assay/collection device comprising an absorbent material capable of collecting the blood sample by capillary action and producing an observable colorimetric pattern from the blood sample; a database of grayscale values and pixel counts corresponding to a plurality of colorimetric patterns produced by a plurality of dried blood sample volumes collected on an assay/collection device; wherein the blood sample is collected and dried on the assay/collection device at a first location and transported to a second location without cold storage or refrigeration, the colorimetric pattern of the dried blood sample is recorded at the second location as a set of data points with the imaging device; and further wherein the executable software program compares the colorimetric pattern of the dried blood sample with the database of grayscale values and pixel counts to derive the volume of the blood sample collected by the assay/collection device.

The subject invention further discloses a system for determining the volume of a blood sample, the fraction of the blood sample volume composed of plasma, and the fraction of the blood sample volume composed of red blood cells, comprising: a computing device comprising executable software; a data storage device; an imagine device; a blood sample assay/collection device comprising an absorbent material capable of collecting the blood sample by capillary action and producing an observable colorimetric pattern from the blood sample; a database of grayscale values and pixel counts corresponding to a plurality of colorimetric patterns produced by a plurality of dried blood sample volumes collected on an assay/collection device; wherein the blood sample is collected and dried on the assay/collection device, the colorimetric pattern of the dried blood sample is recorded as a set of data points with the imaging device; and further wherein the executable software program compares the colorimetric pattern of the dried blood sample with the database of grayscale values and pixel counts to derive i) the volume of the blood sample collected by the assay/collection device, ii) the fraction of the blood sample volume composed of plasma; and iii) the fraction of the blood sample volume composed of red blood cells.

The subject invention further discloses a system for determining the volume of a blood sample, the fraction of the blood sample volume composed of plasma, and the fraction of the blood sample volume composed of red blood cells, comprising: a computing device comprising executable software; a data storage device; an imagine device; a blood sample assay/collection device comprising an absorbent material capable of collecting the blood sample by capillary action and producing an observable colorimetric pattern from the blood sample; a database of grayscale values and pixel counts corresponding to a plurality of colorimetric patterns produced by a plurality of dried blood sample volumes collected on an assay/collection device; wherein the blood sample is collected and dried on the assay/collection device at a first location and transported to a second location without cold storage or refrigeration, the colorimetric pattern of the dried blood sample is recorded as a set of data points with the imaging device at the second location; and further wherein the executable software program compares the colorimetric pattern of the dried blood sample with the database of grayscale values and pixel counts to derive i) the volume of the blood sample collected by the assay/collection device, ii) the fraction of the blood sample volume composed of plasma; and iii) the fraction of the blood sample volume composed of red blood cells.

The subject invention also discloses a system for determining the volume of a blood sample, the fraction of the blood sample volume composed of plasma, and the fraction of the blood sample volume composed of red blood cells, comprising: a computing device comprising executable software; a data storage device; an imagine device; a blood sample assay/collection device comprising an absorbent material capable of collecting the blood sample by capillary action and producing an observable colorimetric pattern from the blood sample; a database of grayscale values and pixel counts corresponding to a plurality of colorimetric patterns produced by a plurality of dried blood sample volumes, volume fractions of plasma within the dried blood sample volume, and volume fractions of red blood cells within the dried blood sample volume collected on an assay/collection device; wherein the blood sample is collected and dried on the assay/collection device, the colorimetric pattern of the dried blood sample is recorded as a set of data points with the imaging device; and further wherein the executable software program compares the colorimetric pattern of the dried blood sample with the database of grayscale values and pixel counts to derive i) the volume of the blood sample collected by the assay/collection device, ii) the fraction of the blood sample volume composed of plasma; and iii) the fraction of the blood sample volume composed of red blood cells.

The subject invention discloses a system for determining the concentration of a target analyte in a blood sample, comprising: a computing device comprising executable software;

a data storage device; an imagine device; a blood sample assay/collection device comprising an absorbent material capable of collecting the blood sample by capillary action and producing an observable colorimetric pattern from the blood sample; a database of grayscale values and pixel counts corresponding to a plurality of colorimetric patterns produced by a plurality of dried blood sample volumes collected on an assay/collection device; wherein the blood sample is collected and dried on the assay/collection device, the colorimetric pattern of the dried blood sample is recorded as a set of data points with the imaging device, further wherein the executable software program compares the colorimetric pattern of the dried blood sample with the database of grayscale values and pixel counts to derive the volume of the blood sample collected by the assay/collection device, wherein the dried blood sample is extracted from the assay/collection device with an extraction solution to produce a fluid sample extract, an assay determines the mass of the target analyte in the fluid sample; and combining the target analyte mass determination with the blood sample volume determination to derive the concentration of the target analyte in the blood sample.

The subject invention discloses a system for determining the concentration of a target analyte in a plasma portion of a blood sample, the method comprising, comprising: a computing device comprising executable software; a data storage device; an imagine device; a blood sample assay/collection device comprising an absorbent material capable of collecting the blood sample by capillary action and producing an observable colorimetric pattern from the blood sample; a database of grayscale values and pixel counts corresponding to a plurality of colorimetric patterns produced by a plurality of dried blood sample volumes, volume fractions of plasma within the dried blood sample volume, and volume fractions of red blood cells within the dried blood sample volume collected on an assay/collection device; wherein the blood sample is collected and dried on the collection device, the colorimetric pattern of the dried blood sample is recorded as a set of data points with the imaging device; further wherein the executable software program compares the the colorimetric pattern of the dried blood sample with the database of grayscale values and pixel counts to derive i) the volume of the blood sample collected by the assay/collection device, ii) the fraction of the blood sample volume composed of plasma, iii) the fraction of the blood sample volume composed of red blood cells; wherein the dried blood sample is extracted from the assay/collection device with an extraction solution to produce a fluid sample extract, an assay determines the mass of the target analyte in the fluid sample, combining the target analyte mass determination with the blood sample volume determination to derive the concentration of the target analyte in the blood sample; and combining the mass of the target analyte, the fraction of the blood sample volume composed of plasma, the fraction of the blood sample volume composed of red blood cells, and the red blood cell partitioning coefficient to derive the concentration of the target analyte in the plasma portion of the blood sample.

In embodiments of the subject invention, the absorbent material incorporated into the assay/collection device comprises cellulose-based paper In other embodiments of the subject invention, the imaging device comprises a digital camera.

In further embodiments of the subject invention, the data points comprise grayscale values and pixel counts.

In additional embodiments of the subject invention, the software program incorporates at least one database correlating the initial volume of blood sample dried onto the assay/collection device with data pertaining to the colorimetric pattern produced by the blood sample, the data comprising grayscale values and pixel counts.

In embodiments of the subject invention, the assay incorporates techniques selected from the group consisting of: chromatography, mass spectrometry, immunoassays, chemical assays, biochemical assays, biological assays, and nucleic acid amplification assays.

In other embodiments of the subject invention, the assay/collection device further comprises at least one extraction marker that is dried onto the absorbent material at known masses and is co-extracted with the target analyte to provide means for normalizing the sample blood volume concentration result.

In further embodiments of the subject invention, the absorbent material incorporated in the assay/collection device comprises a strip with a fill line such that, when the blood sample is collected on the assay/collection device, the strip is contacted with the blood sample for a period of time sufficient for the blood sample to migrate to the fill line.

In embodiments of the subject invention, the computing device is selected from the group consisting of a laptop, a tablet, a smartphone, and a desktop computer.

In embodiments of the subject invention, the terms "substantial" or "substantially" are defined as at least close to (and can include) a given value or state, as understood by a person of ordinary skill in the art. In one embodiment, the terms "substantial" or "substantially" refers to ranges within 10%, preferably within 5%, more preferably within 1%, and most preferably within 0.1% of the given value or state being specified.

There are additional features of the invention that will be described hereinafter and which will form the subject matter of the claims appended hereto. These together with other objects of the invention, along with the various features of novelty, which characterize the invention, are pointed out with particularity in the claims annexed to and forming a part of this disclosure.

BRIEF DESCRIPTION OF THE DRAWINGS

Advantages of the present invention will be apparent from the following detailed description of exemplary embodiments thereof, which description should be considered in conjunction with the accompanying drawings:

FIG. 15 is a graphic showing the FIG. 7 assay/collection device being used to collect a blood sample from a finger prick.

FIG. 17 is a diagrammatic top view of a multi-sample, strip-based assay/collection device, incorporating four of the FIG. 3 devices and a backing, after receiving blood samples.

FIG. 18 is a diagrammatic top view of the FIG. 12 assay/collection device after receiving blood samples.

FIG. 19 is a diagrammatic top view of the FIG. 13 assay/collection device after receiving blood samples.

FIG. 21 is a diagrammatic top view of an imaging device insert.

FIG. 22 is a diagrammatic bottom view of the FIG. 21 insert containing calibration and labeling elements.

FIG. 33 is a diagrammatic front view of a second embodiment of an automatable assay/collection device.

FIG. 34 is the FIG. 33 assay/collection device with the desiccant cartridge removed, leaving a sample extraction assembly.

FIG. 35 is a diagrammatic bottom view of the FIG. 35 desiccant cartridge.

DETAILED DESCRIPTION OF THE INVENTION

Figure 1:
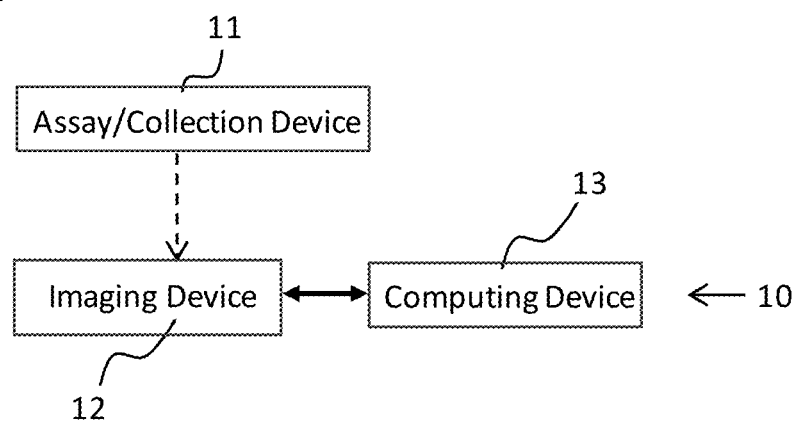
FIG. 1 is a diagram showing three operatively connected components of the system, an assay/collection device, an imaging device and a computing device.

The following will describe, in detail, several embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used and made without departing from the scope and spirit of the invention.

The term "analyte", as used herein, refers to a molecule or compound for which an amount will be measured. Examples of analytes include drugs, hormones, toxins, metabolites, atoms, small molecules, large molecules, peptides, proteins, lipids, carbohydrates, nucleic acids, polymers, viruses, cellular components, and other compounds.

The term "assay", as used herein, refers to an in vitro procedure for analysis of a sample to determine the presence, absence or quantity of one or more analytes.

The term "hematocrit", as used herein, refers to the volume percentage of red blood cells in blood.

The present invention provides a system and method for collecting, transporting and analyzing a blood sample or other fluid sample. The system comprises an assay/collection device, an imaging device operatively connected to the assay/collection device, and a computing device operatively connected to the imaging device, wherein the computing device comprises an executable software program capable of analyzing data points from the imaging device so as to measure various properties of the collected sample, such as the volume and hematocrit of a blood sample collected on the assay/collection device. The software program may also be capable of performing further calculations by incorporating data points obtained from additional devices or procedures.

The method of the invention comprises collecting an approximate volume of sample on the assay/collection device, allowing for the sample to dry in such a way as to allow the device to be transported to a second location without requiring conditions or expenses associated with the transport of non-dried blood samples. For example, the device may be transported to a second location in an addressed envelope without the need for refrigeration or expedited delivery times. The method of the invention further comprises collecting one or more digital images of the sample-containing assay/collection device with the imaging device. After a sufficient number of images have been collected, the dried sample contained on the assay/collection device is subjected to an extraction process converting it into a fluid sample. The fluid sample is then subjected to one or more laboratory analyses and the resulting data is combined with the digital image data (received by the computing device) to derive an assay result.

The invention incorporates the novel feature of imaging dried blood samples and using the data from this imaging to derive the pre-dried volume of the imaged blood sample, determining the total volume of sample as well as the fraction of the volume comprising plasma and the fraction of the volume comprising erythrocytes (red blood cells). This novel feature provides a platform that accommodates further novel device designs and method strategies allowing for the analysis of one or more analytes in dried blood samples with a greater degree of accuracy, precision, sensitivity, specificity and reliability then current systems are able to achieve. In addition, this novel feature provides a platform that accommodates further novel device designs and method strategies allowing for easier sample collection and automatable sample processing.

The novel volume-deriving feature noted above makes use of the surprising observation that the color values of blood samples dried onto certain filter matrices contain information that correlates unambiguously with pre-dried sample volumes. This correlation is surprising for multiple reasons, including the fact that this information is not readily discernable by visual inspection, and that dried blood samples are in a constant state of color change for reasons that are independent of the pre-dried sample volume and may obscure the information relevant to the volume derivation, such as a comparison of color density between two colors having different hues. In addition, the correlation between the color of a dried blood sample and its pre-dried volume is not a direct correlation. Rather it is connected by multiple discreet relationships, such as the relationship between 1) color value and hemoglobin density, 2) hemoglobin density and sample hematocrit, 3) sample hematocrit and sample viscosity, 4) sample viscosity and area dispersion on a collection matrix, and 5) area dispersion and sample volume.

FIG. 1 is a diagram showing three basic components of the system 10. The system comprises an assay/collection device 11 operatively connected to an imaging device 12. The imaging device, in turn, is operatively connected to a computing device 13. In a preferred embodiment, the assay/collection device is used to collect a fluid blood sample that dries after having been collected. The sample is collected and dried in such a way as to create one or more colored areas capable of being recorded by the imaging device. The assay/collection device may collect one or more dried blood samples, and each sample may comprise a plurality of shapes and sizes.

The assay/collection device is operatively connected to the imaging device in such a way as to allow the imaging device to record one or more images of the dried blood sample. In some embodiments, the image is recorded by placing the collection device in direct contact with the imaging device, while in other embodiments the image is recorded by placing the assay/collection device in close proximity to the imaging device.

The imaging device is operatively connected to a computing device, wherein the computing device comprises an executable software program and databases capable of analyzing data points from the imaging device. The computing device may comprise one or more hardware components and be linked to one or more additional devices or systems.

In embodiments of the subject invention, the computing devices include communication devices (such as a bus), a CPU/processor, a main operating memory, and a storage memory. Embodiments of the CPU/processor may include processors, microprocessors, multi-core processors, microcontrollers, system-on-chips, field programmable gate arrays (FPGA), application specific integrated circuits (ASIC), application specific instruction-set processors (ASIP), or graphics processing units (GPU). The host servers and the mobile computing devices store computer retrievable information and software executable instructions and may include solid state, magnetic, or optical recording mediums. The input device of the computing devices may include a keyboard, a mouse, a pen, a microphone combined with voice recognition software, a camera with image recognition software, a multi-point touch screen, a bar code scanner, or an SKU scanner. The underlying architecture of the system may be implemented using one or more computer programs, each of which may execute under the control of an operating system, such as Windows, OS2, DOS, AIX, UNIX, MAC OS, iOS, ChromeOS, Android, and Windows Phone or CE.

Figure 2:
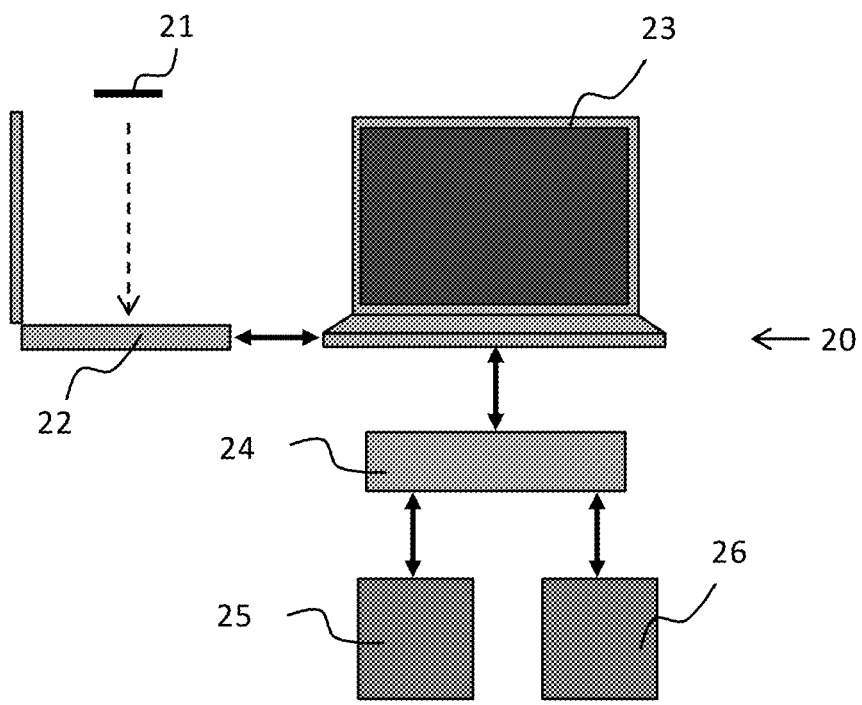
FIG. 2 is a diagram showing operatively connected components of the system, with the imaging device comprising a flatbed digital scanner and the computing device comprising a laptop computer connected to additional components.

FIG. 2 is a diagrammatic view of the system 20 showing an assay/collection device 21 in the process of being placed onto an imaging instrument represented by an accessorized digital flatbed scanner 22. The scanner is operatively connected to a computing instrument represented in the figure as a laptop computer 23 connected to an additional computer 24 such as a server. The additional computer is in turn connected to additional instruments (24 and 25) that may be used to conduct assays on the sample and transmit the results of these assays to the computer for analysis in conjunction with the data derived from the imaging device.

The assay/collection device allows for the rapid, simple collection of a volume of blood. In a preferred embodiment, the assay/collection device comprises a unit of absorbent wicking material (the sample region) capable of fluid sample collection by capillary action. The sample region may be comprised of any suitable absorbent material including, but not limited to, Whatman 903 filter paper, Whatman DMPK filter paper, Whatman FTA filter paper, Ahlstrom Grade 226 filter paper and/or Munktell TFN filter paper.

Figure 3:
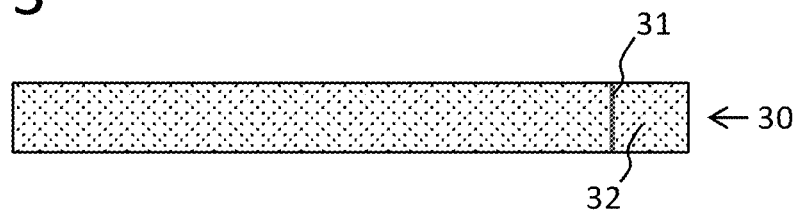
FIG. 3 is the diagrammatic top view of a first embodiment of a strip-based assay/collection device.
Figure 4:
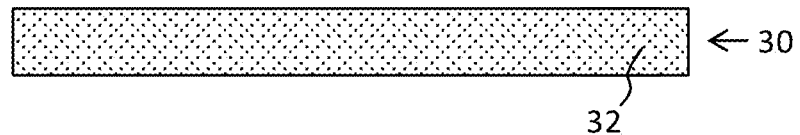
FIG. 4 is a diagrammatic bottom view of the FIG. 3 assay/collection device.
Figure 5:
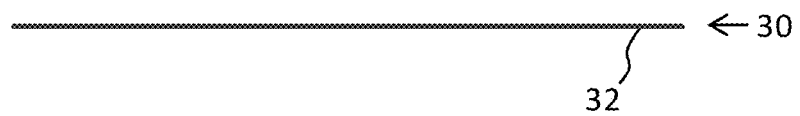
FIG. 5 is a diagrammatic side view of the FIG. 3 assay/collection device.

FIG. 3 illustrates a first embodiment of the assay/collection device 30, comprised of a strip of wicking material incorporating a fill line 31 on one end. FIG. 3 is a diagrammatic top view where the fill line is visible and is used to define the sample region 32 of the device. FIG. 4 is a diagrammatic bottom view of the FIG. 3 device and FIG. 5 is a diagrammatic side view of the FIG. 3 device. In a preferred embodiment, the fill line is printed onto the strip using ink that will not interfere in assays using the collection device. In a preferred embodiment, the strip comprises a width in the range of 4-8 mm and the sample region comprises an area in the range of 16-64 mm^2.

A significant problem with conventional DBS cards and other current dried blood collection devices is that target analytes must be extracted from the collection matrix and these extractions do not necessarily occur with a quantitatively predictable efficiency, leading to variability in test results. The present invention addresses this problem by providing device that can accommodate the quantitative incorporation of dried extraction markers onto the sample region. These markers can then serve as internal references to measure extraction efficiencies, which can then be incorporated into the calculation of test results.

In a preferred embodiment, the extraction markers are dissolved into a solution which is then quantitatively sprayed or otherwise applied onto the sample region of a collection device. For the strip-based collection devices, an effective way to incorporate the spraying step into the manufacturing process is to construct the devices initially from sheets or rolls that are subsequently cut into the strips.

Figure 6:
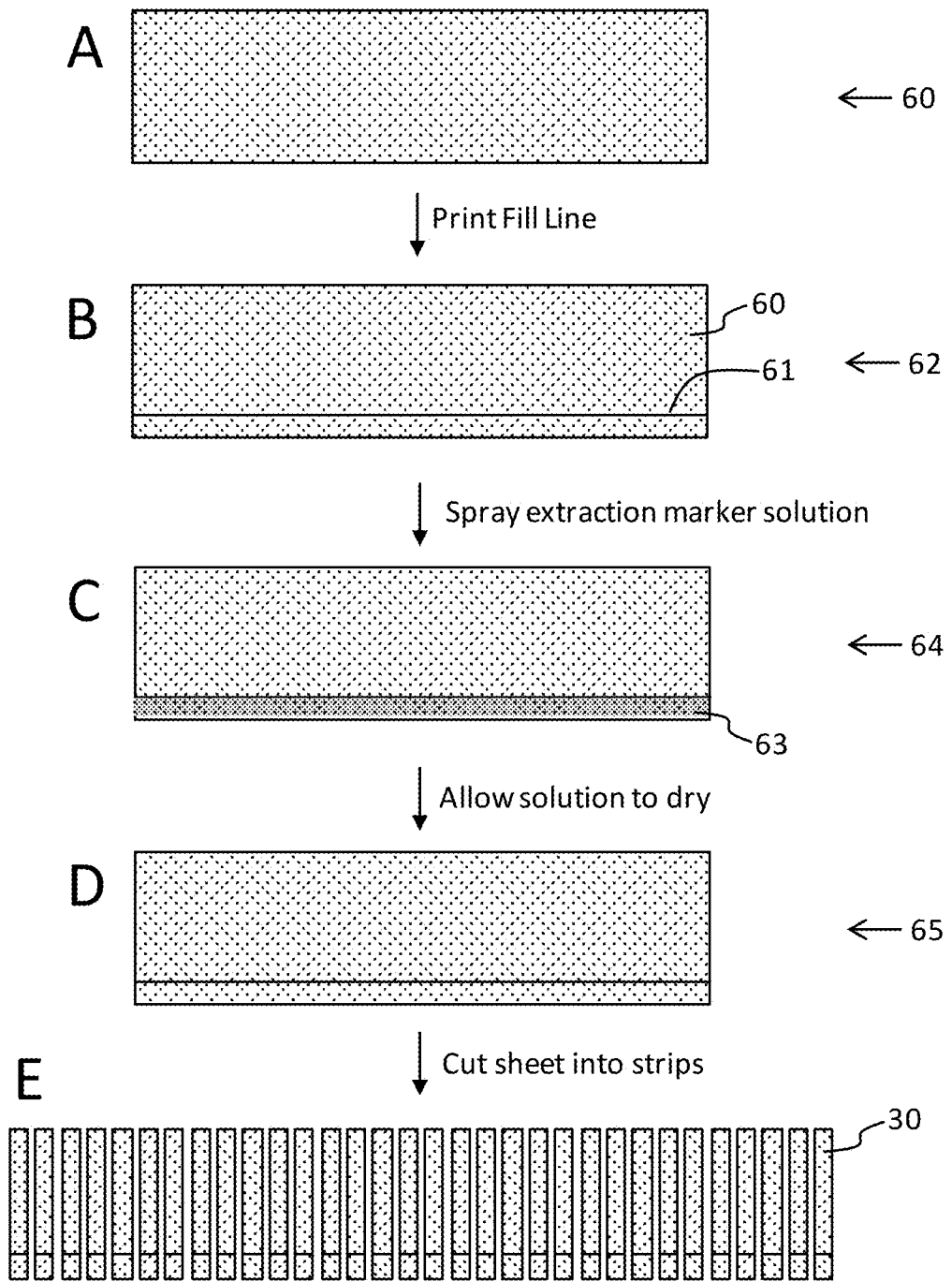
FIG. 6 is a flow diagram illustrating the production of a batch of FIG. 3 assay/collection strips.

FIG. 6 shows a sequence of diagrammatic top views that illustrate the manufacturing of the assay/collection devices described in FIG. 3, wherein the devices incorporate a quantitative amount of one or more extraction markers in the sample region. Step A shows a sheet of wicking material 60 serving as the starting sheet. A fill line 61 is then printed onto the sheet as shown in Step B creating the interim sheet 62. As shown in Step C the wicking material is then sprayed with a quantitative amount of extraction marker solution 63 (depicted as a gray coloring on the wicking material) in such a way as to incorporate a defined amount of extraction markers per volume of absorbent material, thus creating interim sheet 64. The extraction marker solution is then allowed to dry, resulting in a pre-cut sheet of collection devices 65 shown in Step D. In the final step, the sheet is cut into strips as shown in Step E, each strip serving as a sample strip 30 that contains a quantitative amount of extraction marker material dried onto the sample region.

Figure 7:
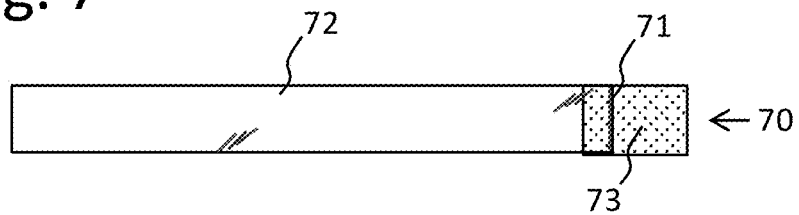
FIG. 7 is the diagrammatic top view of a second embodiment of a strip-based assay/collection device having a solid support.
Figure 8:
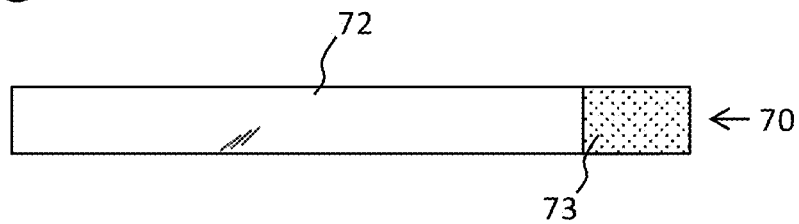
FIG. 8 is a diagrammatic bottom view of the FIG. 7 assay/collection device.
Figure 9:
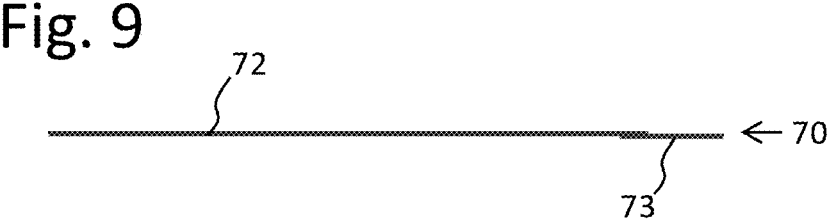
FIG. 9 is a diagrammatic side view of the FIG. 7 assay/collection device.

FIG. 7 illustrates a second embodiment of the assay/collection device 70, comprised of a truncated strip of wicking material attached to a non-absorbent support. FIG. 7 is a diagrammatic top view where the fill line 71 is visible within the overlapping space between the support 72 and the wicking material 73. The non-overlapping portion of the wicking material defines the sample region. In this embodiment, the support is comprised of a transparent material, such as transparent plastic, enabling the fill line to be printed on either the support or the wicking material. In other embodiments, the support may be opaque and the fill line may be printed on the edge of the support. In a preferred embodiment, the sample region is connected to the support through any suitable means including, but not limited to, an adhesive. FIG. 8 is a diagrammatic bottom view of the FIG. 7 device and FIG. 9 is a diagrammatic side view of the FIG. 7 device. In a preferred embodiment, the strip comprises a width in the range of 4-8 mm and the sample region comprises an area in the range of 16-64 mm^2.

Figure 10:
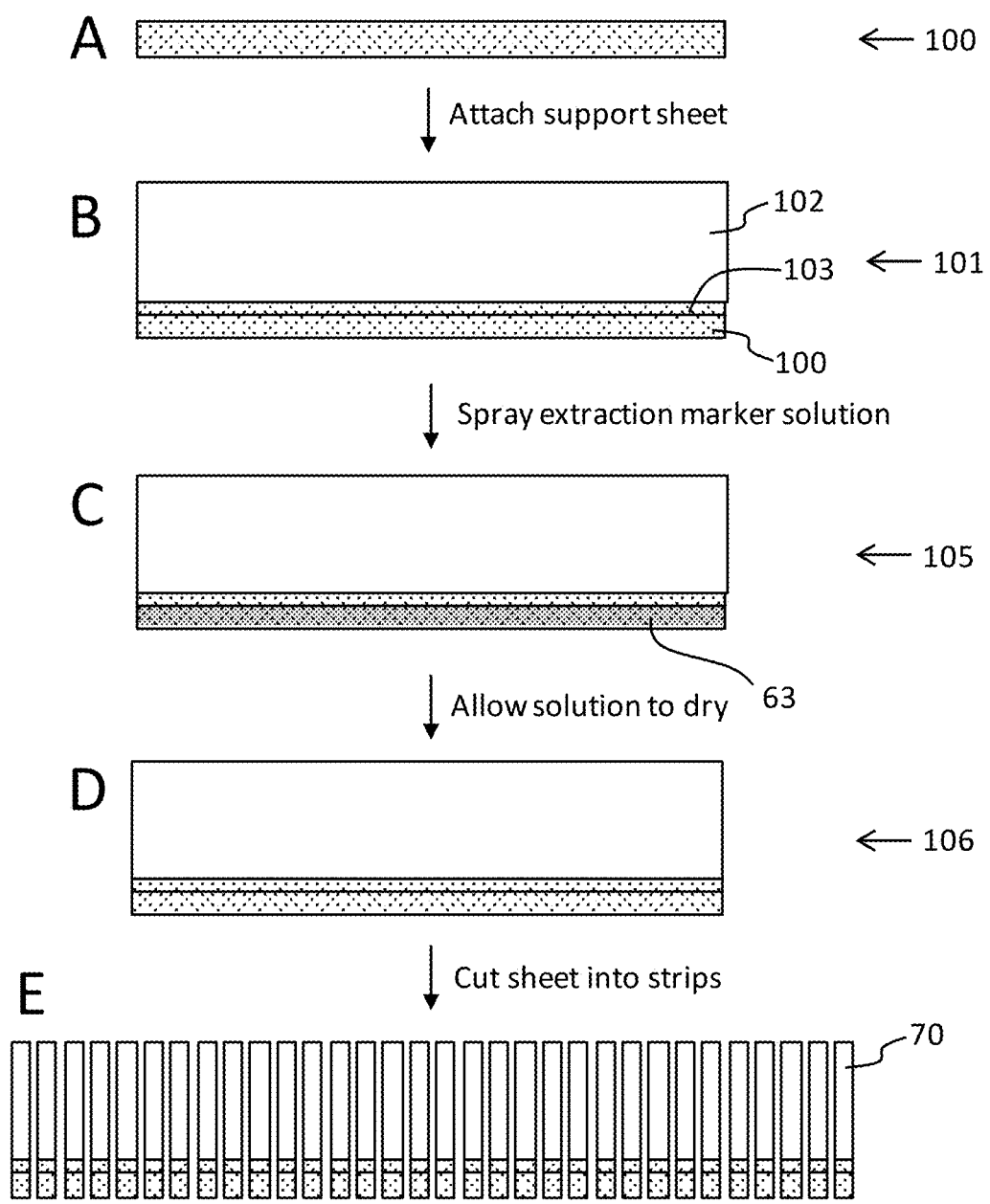
FIG. 10 is a flow diagram illustrating the production of a batch of FIG. 7 assay/collection strips.

FIG. 10 shows a sequence of diagrammatic top views that illustrate the manufacturing of the assay/collection devices described in FIG. 7, wherein the devices incorporate a quantitative amount of one or more extraction markers in the sample region. Step A shows a long rectangular piece of wicking material 100 that will ultimately provide the sample region for the collection devices. As shown in Step B, this material is attached to a long rectangular sheet of material 102 that will ultimately provide the support for the collection devices, thus creating interim sheet 101. A fill line 103 is printed along the edge of the support that overlaps the wicking material. As shown in Step C the wicking material is then sprayed with a quantitative amount of extraction marker solution 63 (depicted as a gray coloring on the wicking material) in such a way as to incorporate a defined amount of extraction markers per volume of absorbent material, thus creating interim sheet 105. The extraction marker solution is then allowed to dry, resulting in a pre-cut sheet of collection devices 106 shown in Step D. In the final step, the sheet is cut into strips as shown in Step E, each strip serving as a sample strip 70 that contains a quantitative amount of extraction marker material dried onto the sample region.

The manufacturing processes outlined in FIG. 6 and FIG. 10 accommodates a means for reliably and efficiently depositing a quantitative amount of extraction marker material onto a defined area of wicking material. This process can be accomplished with currently available manufacturing equipment, eliminating the time and costs associated with having to develop customized manufacturing equipment and procedures. For example, the spraying step shown in FIG. 6, Step C and 10, Step C can be accomplished with a Biodot Airjet HR Nanoliter Aerosol Dispenser, and the cutting step shown in FIG. 6, Step E and 10, Step E can be accomplished with a Biodot CM4000 Guillotine Cutter. In some embodiments, the strips are first produced before the application of extraction markers and the markers are then applied to the sample region by spotting techniques and equipment.

Extraction markers may be selected based on the analytes of interest or the assay method used for analyzing the extract. Examples of extraction markers include, but are not limited to, deuterium-labeled compounds (which may be used in conjunction with mass spectrometry techniques) amplifiable nucleic acid analytes (which may be used in conjunction with nucleic acid amplification techniques such as polymerase chain reaction assays) and proteins (which may be used in conjunction with immunoassay or chemistry techniques). In some embodiments, the extraction marker is a derivative of the analyte of interest. For example, a collection device designed to measure methadone concentrations in blood may incorporate deuterium-labeled methadone as an extraction marker. In other embodiments, one or more compounds may be used as extraction markers based on properties of those compounds that would predict the extraction efficiency of the analyte of interest. For example, a set of deuterium-labeled compounds (drugs, amino acids, vitamins, metabolites) representing a spectrum of molecular properties that influence extraction efficiency (size, polarity, etc.) may be collectively dried onto the sample region. The extraction efficiency of the analyte of interest may then be determined based on a weighting of the extraction markers, with greater weighting being given to those extraction markers that most resemble the analyte of interest or are shown experimentally to extract with an efficiency that best predicts the extraction efficiency of the analyte of interest. The determination of extraction efficiency may incorporate computational methods such as supervised machine learning or other artificial intelligence methods.

In some embodiments, assay/collection devices incorporating extraction markers may be used to analyze target analytes in non-blood samples such as urine and saliva.

The strip-based assay/collection devices shown in FIGS. 3 and 7 may be attached to a backing to enable easier handling, provide a location to place information, group multiple devices together into a single multi-strip device or perform some other function. The backing may be comprised of any suitable material, such as paper, cardboard or plastic. The strips may be attached to the backing in a number of different ways including, but not limited to, the use of an adhesive or the addition of a pocket to the backing. In some embodiments the strips may be permanently attached to the backing while in other embodiments the strips may be removable from the backing. Information placed onto the backing may include barcodes, alphanumeric labels and/or written information indicating, for example, the identity of the individual supplying the sample, the date of sample collection, the location of sample collection, analytes to be tested for, the location where tests will be performed, or other information.

Figure 11:
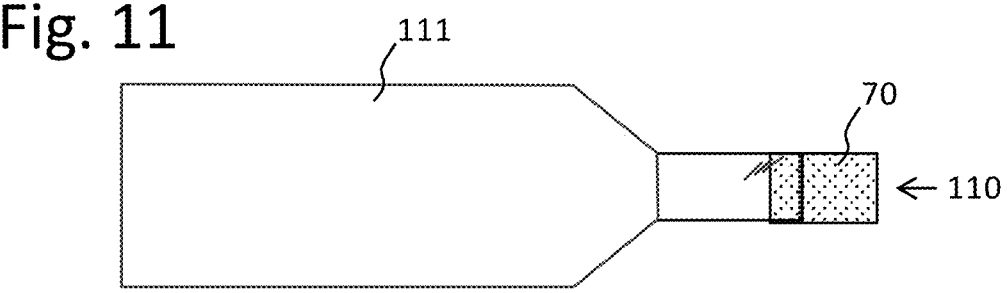
FIG. 11 is a diagrammatic top view of a single-sample, strip-based assay/collection device incorporating one of the FIG. 7 devices and a backing.
Figure 12:
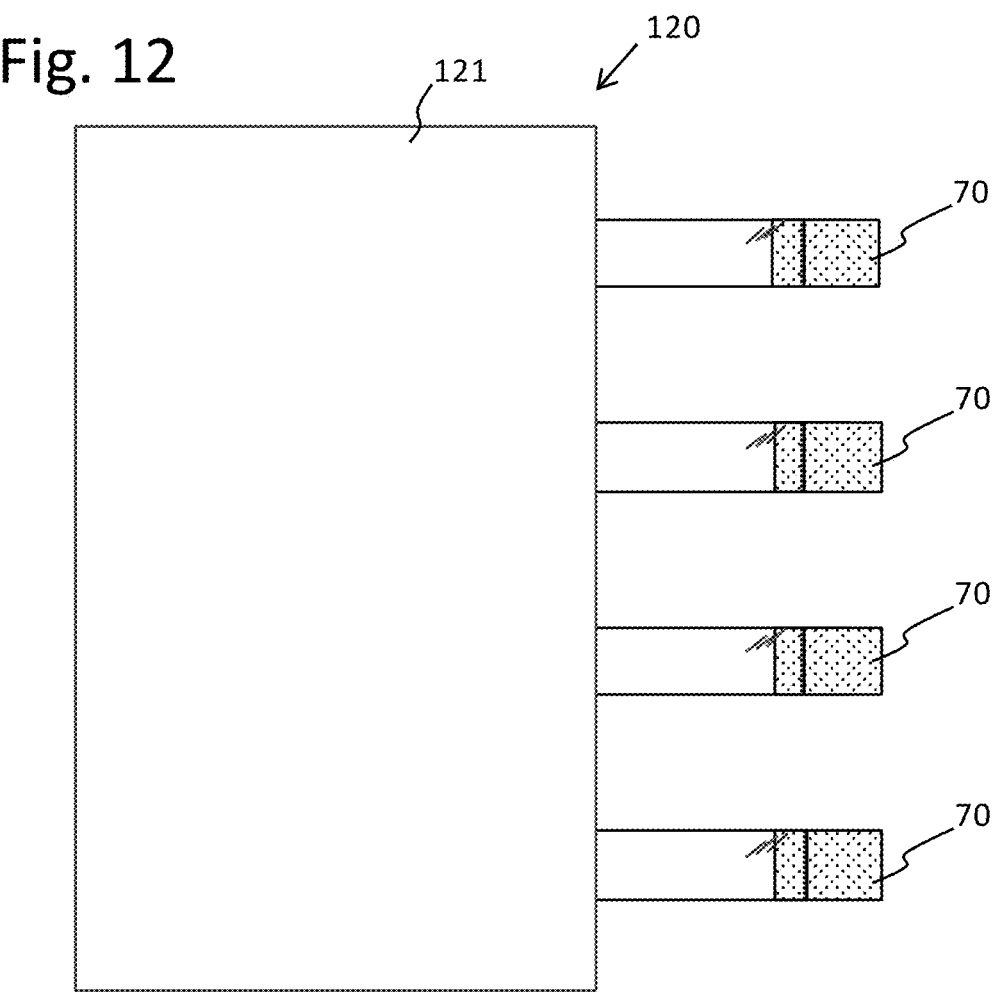
FIG. 12 is a diagrammatic top view of a multi-sample, strip-based assay/collection device incorporating four of the FIG. 7 devices and a backing.

FIG. 11 is a diagrammatic top view of the FIG. 7 assay/collection device inserted into the pocket of a backing 111 to form a backed, removable single-strip-based assay/collection device 110. FIG. 12 is a diagrammatic top view of four FIG. 7 collection devices inserted into the pockets of a rectangular backing 121 to form a backed, removable multi-strip-based assay/collection device 120.

In addition to the strip-based assay/collection devices described above, other embodiments of the assay/collection device comprise a wider sheet of wicking material configured to collect blood samples in the form of spots, similar to conventional dried blood spot collection cards. These "spot-based" devices may contain markings such as circles, to identify the location or locations where samples are applied.

For conventional DBS cards, dried samples are typically processed by punching a small hole inside the area of the sample spot and extracting the punched out sample-containing paper. An analysis of the entire spot requires the user to apply a known volume of blood to the card using a volume-measuring instrument such as a pipettor. These instruments are expensive, require a certain amount of skill to operate, and add a challenging and cumbersome step to the collection process. Consequently, whole spot analysis is seldom used with conventional DBS cards. The present invention allows for whole spot analyses while eliminating the need to apply a measured volume of blood. In addition, the collection devices can incorporate perforations around the spotting locations to eliminate the need for cutting tools to punch out the dried sample.

Figure 13:
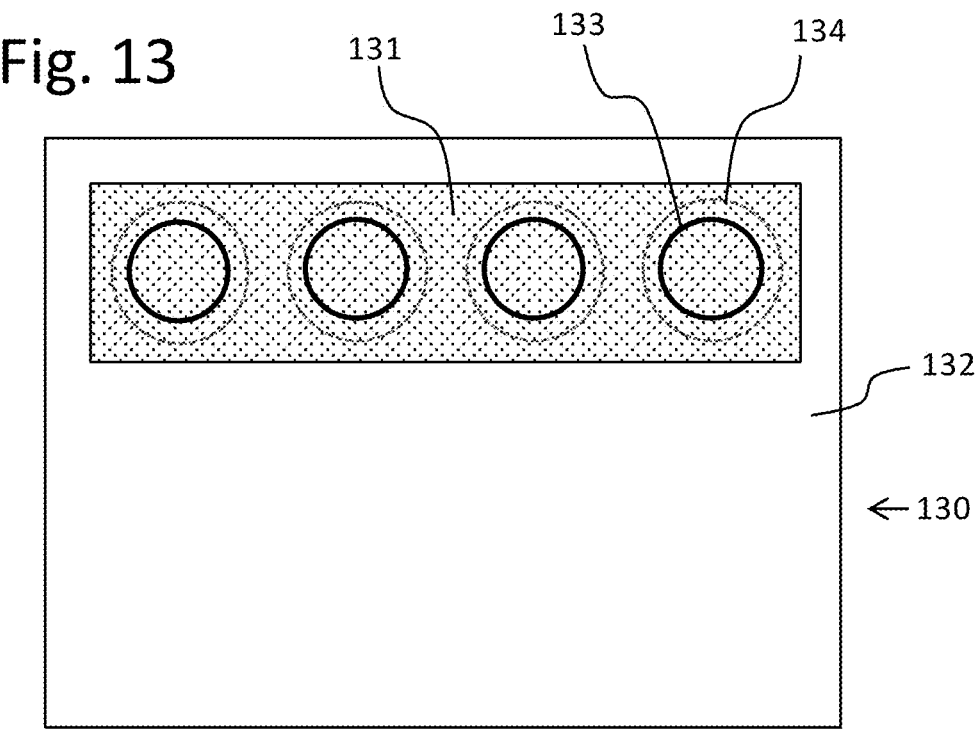
FIG. 13 is a diagrammatic top view of a first embodiment of a multi-sample, spot-based assay/collection device.
Figure 14:
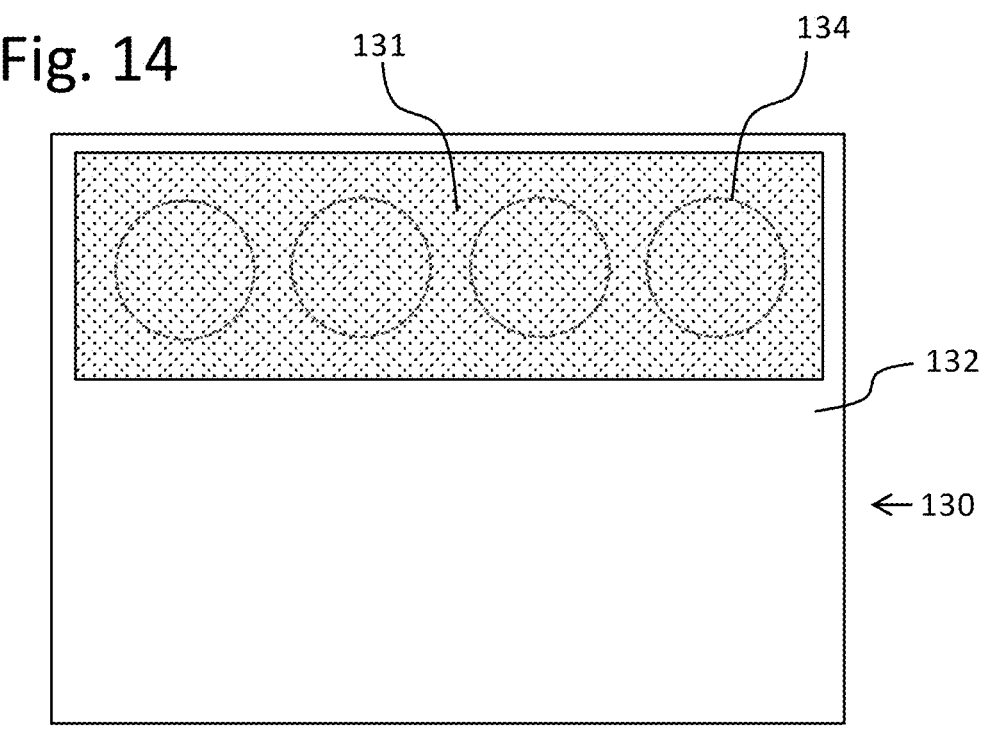
FIG. 14 is a diagrammatic bottom view of the FIG. 13 assay/collection device.

FIG. 13 illustrates a spot-based assay/collection device 130 configured for whole spot collection. The device accommodates up to four blood spots (other embodiments may accommodate a larger or smaller number of spots). FIG. 13 is a diagrammatic front view of the device showing a rectangular sheet of wicking material 131 attached to a backing 132 designed to frame the material, thereby conferring additional structural support. Four circles 133 are printed onto the wicking material to designate the location for each sample spot. Surrounding each circle is a perforation 134 allowing for easy removal of the sample for subsequent analysis. FIG. 14 is a diagrammatic back view of the FIG. 13 device. In a preferred embodiment, the circles are printed onto the sheet using ink that will not interfere in assays using the collection device and comprise a size in the range of 10-20 mm in diameter.

In a preferred embodiment, extraction markers applied to the spot-based assay/collection device are applied inside the area defined by the printed circles In another embodiment of the spot-based assay/collection device the perforations are omitted. In still another embodiment of the spot-based collection device, the perforated circles are first removed from the sheet and incorporated into a non-absorbent housing.

The strip-based assay/collection devices described herein provide a rapid and simple way for collecting a small volume of blood, considerably easier than current methods that rely on spotting techniques. In a preferred embodiment, a small volume of blood is first generated (such as by pricking a finger with a lancet) then the sample region of a strip-based assay/collection device is brought into contact with the blood and contact is maintained until a sufficient amount of blood has migrated onto the sample region. FIG.

15 illustrates the process of collecting blood from a finger with an assay/collection device produced as described in FIG. 7. Step A depicts a sample donor's finger 151 after having been pricked, resulting in the formation of a drop of blood 152. An assay/collection device 70 is shown just prior to making contact with the blood. Step B shows the collection device after contact has been made with the blood resulting in the blood migrating onto the sample region of the device through capillary action. Step C shows a blood sample-containing assay/collection device 150 being retracted from the finger with a sufficient amount of blood collected onto the sample region (determined by the visual observation of the blood migrating up to the fill line).

Figure 16:
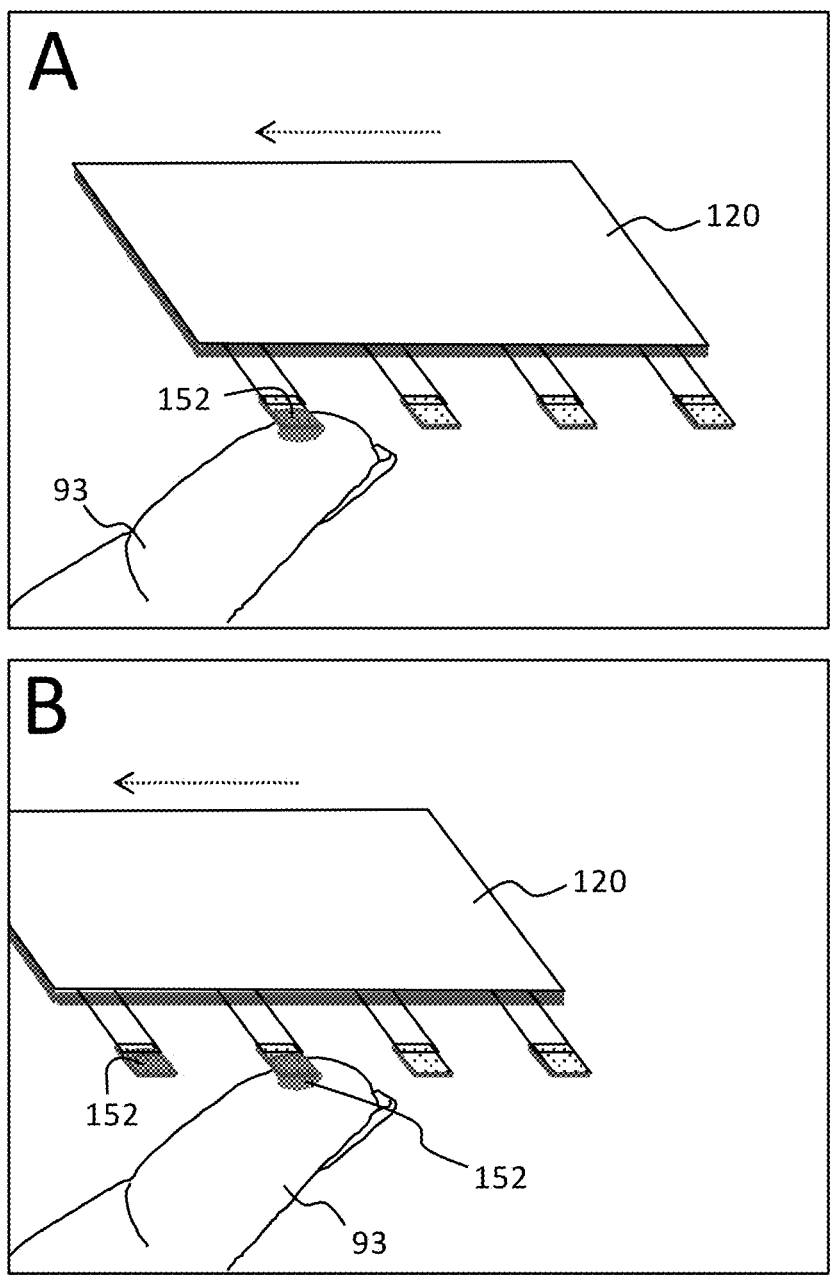
FIG. 16 is a graphic showing the FIG. 12 assay/collection device being used to collect a blood sample from a finger prick.

FIG. 16 illustrates the process of collecting multiple blood samples from a pricked finger using an assay/collection device such as the one described in FIG. 12. Step A shows blood 152 migrating onto the sample region of one of the strips of the device 120. Once a sufficient amount of blood is collected the device is then moved in such a way as to allow contact with a new strip. Step B shows a stage in this process wherein a sufficient amount of blood has been collected on the first strip and the device has been moved in position to collect blood onto the second strip. This process may repeat until all strips on the device have received a sufficient amount of sample.

Assay/collection devices with collected sample can be easily and cost-effectively sent to a second location for analysis. In some embodiments, the blood sample collected on the assay/collection device is allowed to dry before the device is packaged for shipment. Drying may occur by allowing the device to remain at room temperature for several hours, or may occur in an accelerated manner through the use of a drying device that employs mechanisms such as fans or heaters. In other embodiments, the device is packaged before the sample dries, in which case the packaging may contain desiccant or other material that facilitates drying within the contained package.

FIG. 17 is a diagrammatic top view showing dried blood samples 172 collected onto a dried-sample-containing, backed multi-strip assay/collection device 170 incorporating strips produced as described in FIG. 6. FIG. 18 is a diagrammatic top view showing dried blood samples 172 collected onto a dried-sample-containing, backed multi-strip assay/collection device 180 incorporating strips produced as described in FIG. 10. FIG. 19 is a diagrammatic top view showing dried blood samples 172 collected onto a dried-sample-containing, backed multi-spot assay/collection device 190.

In some embodiments, the invention further comprises a sample collection kit containing one or more assay/collection devices and one or more accessory components including, but not limited to, lancets and other items used for generating a pinprick of blood (e.g. a lancing device, alcohol swabs, latex gloves) postage-paid addressed envelopes, instructions and laboratory documentation.

The invention further comprises an imaging device upon which the sample-containing assay/collection device may be placed for imaging and analysis. The device comprises an imaging instrument (such as a scanner comprising a digital camera and light source), operatively connected to a computing device (such as a tablet, laptop, or desktop computer) wherein the computing device comprises an executable software program capable of collecting and analyzing data from the imaging instrument. In a preferred embodiment, the imaging instrument is used to collect one or more digital images of a sample-containing sample region which may then be received by the computing device (as a set of data points) for subsequent analysis. The imaging device may also be used to collect one or more images of an information-containing label or tag associated with the collection device. In a preferred embodiment, the imaging device is used to measure area and grayscale value units associated with the dried sample, and use these measurements to determine the hematocrit level and volume of a blood sample originally collected by the device.

In a preferred embodiment, the imaging device contains a digital camera. The camera captures digital images with an image sensor and light source. Examples of image sensors include, but are not limited to, charge coupled devices (CCD) or complementary metal oxide semiconductors (CMOS), comprising an array of photo sites (also referred to as photo sensors, photo detectors, pixel sensors, or pixel sites). Signals are generated in the form of photons (from the light source) reflecting off the test area and into a photosite within the image sensor. Photons entering a photosite are converted to a proportional number of electrons, which are then measured and assigned a numerical value known as a "grayscale" value. The grayscale value is finally mapped to a location on a two-dimensional grid (based on the location of the photosite within the image sensor), which ultimately defines the captured image. Thus, the collection device is converted to a grid of numerical values, wherein each value can be mapped to a precise location on the device. In a preferred embodiment, the image sensor contains sufficient photo sites to produce a minimum of 300,000 grayscale values per captured image. In another preferred embodiment, each photosite is able to capture multiple gray scale levels, such as in the case of image sensors that are Fovean sensors.

In a preferred embodiment, the imaging device contains one or more color calibration elements. These elements comprise an area of material with one or more defined color values that can be captured in the same image with one or more assay/collection devices and used to provide an objective reference for the grayscale data collected by the image. The color calibration elements may also be imaged before or after the imaging of a collection device for calibration and quality control purposes. In other embodiments, color calibration elements are placed onto the assay/collection device in addition to, or in lieu of, placement onto the imaging device.

Figure 20:
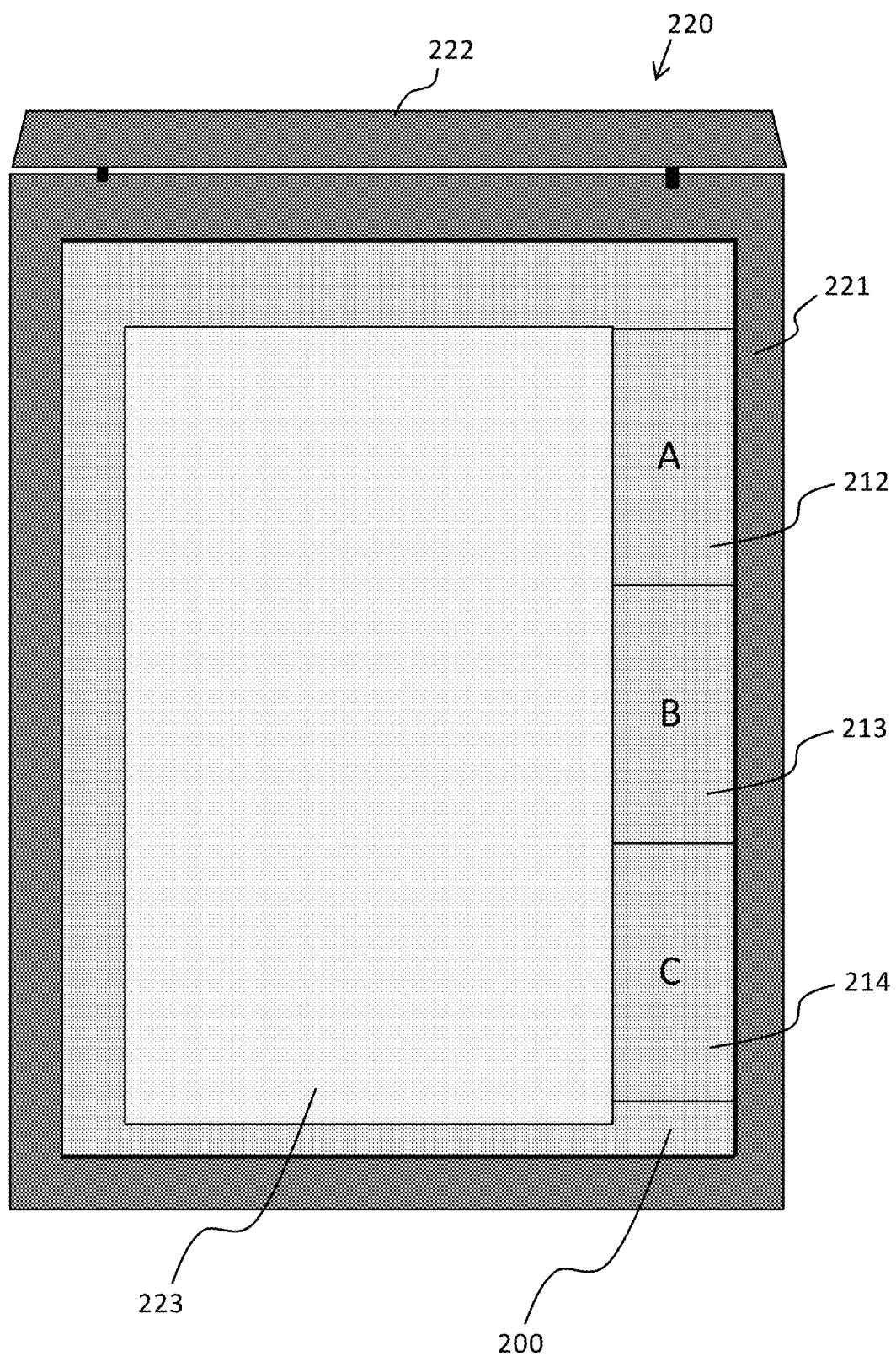
FIG. 20 is a diagrammatic top view of a scanner-based imaging device.

One embodiment of the imaging device comprises a flatbed scanner operating in conjunction with an insert containing calibration and labeling elements. FIG. 20 illustrates one such embodiment. The figure shows a diagrammatic top view of an imaging device 220 comprising a digital flatbed scanner 221 and insert 200 configured to accommodate the 4-sample multi-strip and multi-spot assay/collection devices shown in FIGS. 17-19. The insert is designed to fit over the scanner's plate 223 and be sufficiently flat so as to allow the scanner lid 222 to close appropriately. The top side of the insert incorporates labeled sections (212, 213 and 214) indicating locations where one or more assay/collection devices may be placed for imaging. FIG. 21 is a diagrammatic top view of the FIG. 20 insert without the scanner, providing a clearer view of the opening 205 that allows access to the scanner plate. FIG. 22 is a diagrammatic bottom view of the FIG. 21 insert showing the elements of the insert that are imaged with the assay/collection devices. Alphabetically labeled sections (202, 203 and 204) correspond to the labeling on the top side of the insert, and also incorporate numerical labels to individually identify each strip or spot in the multi-strip or multi-spot assay/collection device. A color calibration target 201 is shown affixed to the insert.

Figure 23:
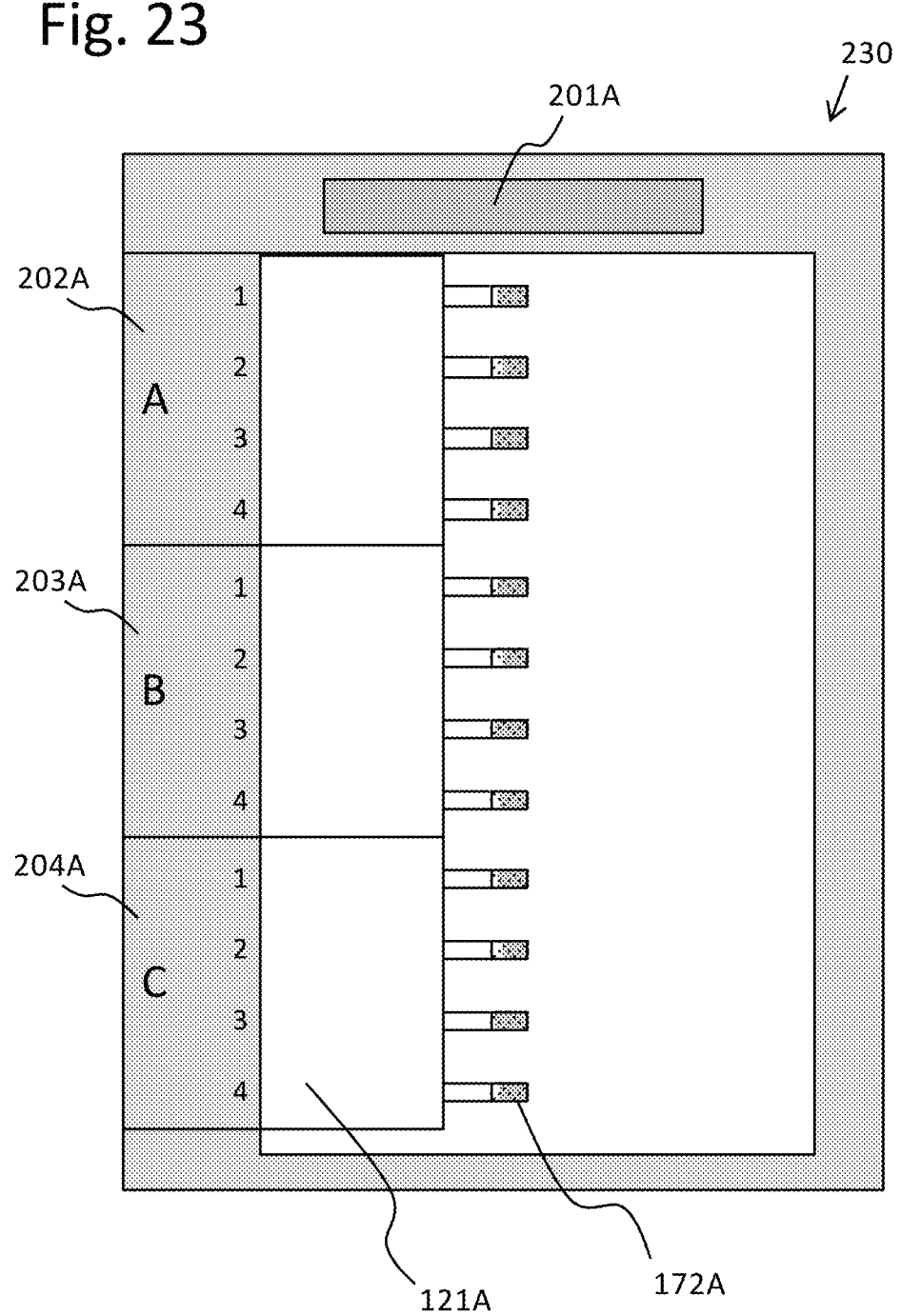
FIG. 23 is a digital image of assay/collection devices recorded with the FIG. 22 imaging device.
Figure 24:
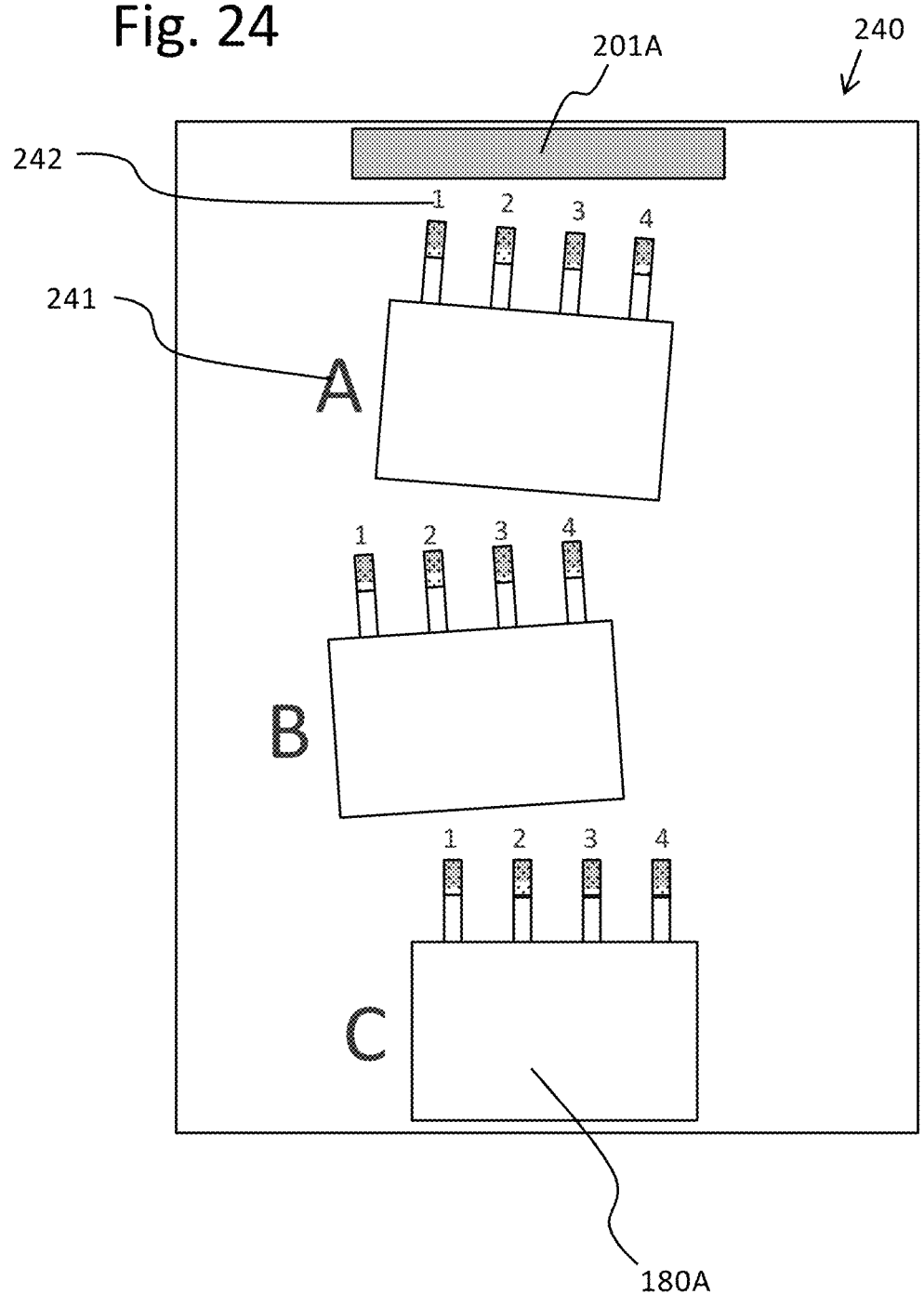
FIG. 24 is a digital image of assay/collection devices recorded with an imaging device containing no insert and incorporating software-generated labeling elements.

The imaging device is used to record one or more digital images of the dried-sample-containing assay/collection devices and use this digital data to determine the initial volume of (liquid) blood applied to the device. For the scanner/insert configuration described above, a typical procedure would be to place one or more devices onto the scanner at locations designated by the sections shown on the insert, close the scanner lid and initiate the scanning process, resulting in one or more digital images. FIG. 23 shows an example of a scanned digital image in which three dried-sample-containing multi-strip assay/collection devices were placed onto an imaging device and recorded. The resulting image provides a set of information for each of the dried blood samples captured in the image. This information includes:

1. The number of pixels comprising the dried blood spot along with the grayscale values for each of these pixels
2. The grayscale values on the calibration target
3. An alphanumeric identifier unique to each sample
4. Any information included on the device backing In some embodiments, the labeling of the devices in the image may be accomplished with the software rather than a labeled insert. FIG. 24 shows an example of a scanned digital image in which three dried-sample-containing multi-strip assay/collection devices were placed onto an imaging device with no insert. To accomplish the labeling, the software superimposed letters and numbers onto the devices it located via mapping functions.

The invention further comprises a computing device, wherein the device comprises an executable software program capable of analyzing data points from the imaging device so as to measure various properties of the collected sample. The software program may also be capable of performing further calculations by incorporating data points, such as assay data points, obtained from additional devices or procedures. In a preferred embodiment, the computing device receives data points from the imaging device and uses these data points to calculate the total volume of blood initially collected on the collection device (prior to a drying step) and the percentage of the total volume attributable to red blood cells in the sample (i.e. sample hematocrit).

The computing device may also receive certain assay data points to calculate the extraction recovery of a target analyte (based on the extraction recovery of one or more extraction markers contained on the collection device). In a preferred embodiment, the computing device comprises one or more databases.

In some embodiments, the computing device comprises (or is linked to) a database containing information related to the erythrocyte partitioning coefficient of target analytes, and uses this database to calculate the concentration of target analytes contained within the plasma or serum portion of the blood sample.

The invention further comprises a means for converting a dried sample (contained on the assay/collection device) into a liquid extract suitable for one or more assays. In a preferred embodiment, the sample containing portion of the device is placed into a suitable container (tube, microwell, vial etc.) and a defined volume of extraction fluid is added to the container so that the sample-containing portion of the device becomes submerged into the extraction fluid. In some embodiments, the sample containing portion of the collection device is first separated from the device and placed into the container. The container is then subjected to a physical agitation process (e.g. shaking, vortexing, sonicating) allowing for the components of the dried sample to become dissolved into the extraction fluid. In a preferred embodiment, the container is placed into a sonicator bath and subjected to sonication. After a sufficient period of time undergoing sonication, a sample extract is generated. In some embodiments, the sample extract is further processed, such as by filtration, centrifugation and/or solid-phase extraction, to remove insoluble matter, concentrate target analytes and/or otherwise render the extract more suitable for analysis.

Figure 25:
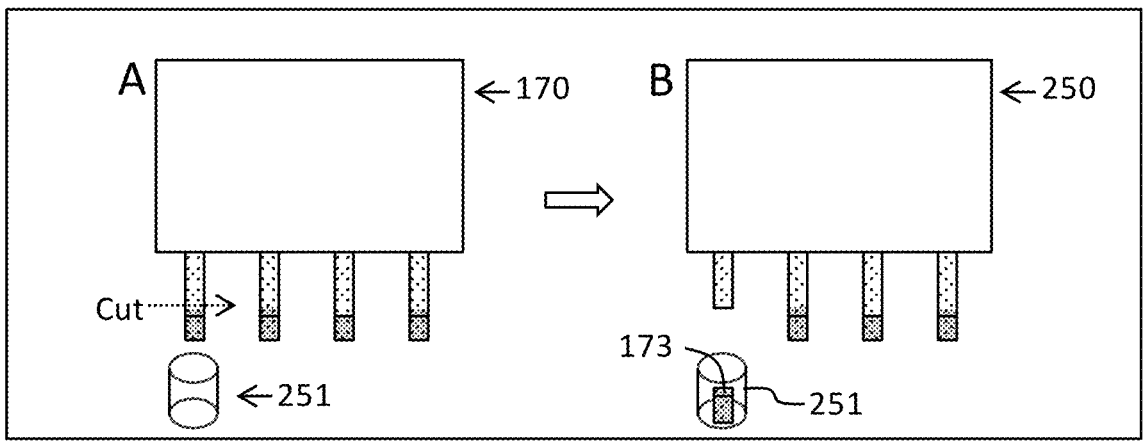
FIG. 25 is a graphic of the FIG. 17 sample-containing assay/collection device showing the process of transferring one of the dried blood samples into an extraction vial.

FIG. 25 illustrates the process of transferring into a container 251 a dried-sample-containing portion of the FIG. 17 assay/collection device. Step A shows a strip on the device 170 in the process of being cut just above the area containing sample. Step B shows the sample-containing piece 173 after being cut from the device and placed into the container. Because the cutting step occurs in the non-sample portion of the strip, the cutting instrument does not have to be cleaned or decontaminated before cutting a strip containing a different sample.

Figure 26:
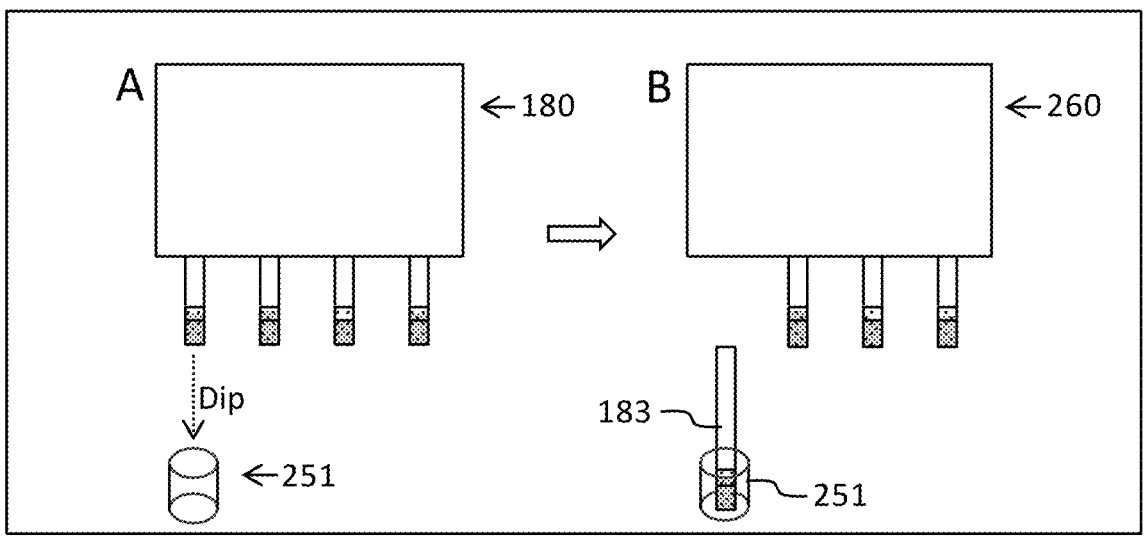
FIG. 26 is a graphic of the FIG. 18 sample-containing assay/collection device showing the process of transferring one of the dried blood samples into an extraction vial.

FIG. 26 illustrates the process of transferring into a container 251 a dried-sample-containing portion of the FIG. 18 assay/collection device. Step A shows a strip on the device 180 in the process of being removed from the device and dipped into the container. Step B shows the sample-containing strip 183 after being removed from the device and dipped into the container. This approach eliminates the inconveniences and potential cross-contamination issues associated with a cutting step.

Figure 27:
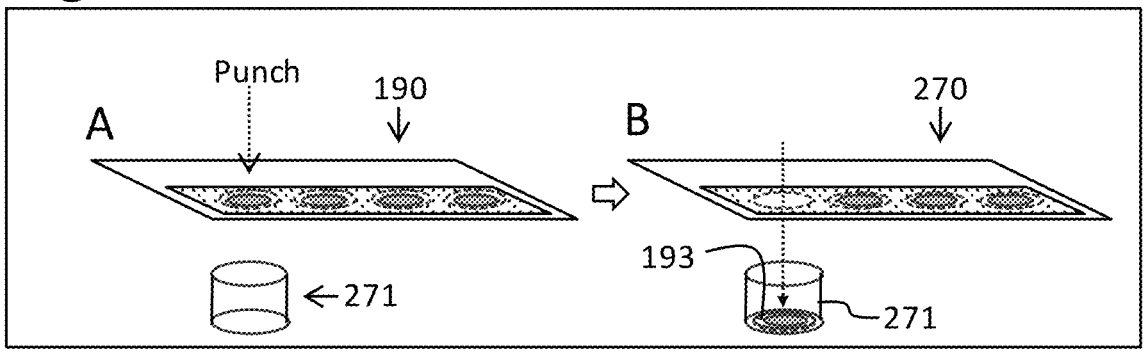
FIG. 27 is a graphic of the FIG. 19 sample-containing assay/collection device showing the process of transferring one of the dried blood samples into an extraction vial.

FIG. 27 illustrates the process of transferring into a container 271 a dried-sample-containing portion of the FIG. 19 assay/collection device. Step A shows a perforated circle on the device 190 in the process of being punched out of the device. Step B shows the sample-containing piece 193 after being punched from the device and placed into the container. This approach eliminates the inconveniences and potential cross-contamination issues associated with a cutting step.

The invention further comprises a method for subjecting the sample extract to one or more assay procedures including, but not limited to, procedures incorporating chromatography, mass spectrometry, immunoassays, chemical assays, biochemical assays, biological assays, and nucleic acid amplification assays. In some embodiments, the sample extract is subjected to optical density or colorimetric analysis with a photo-optic instrument (such as a spectrophotometer or microplate reader) to provide information related to the efficiency of the extraction process. Following the completion of the imaging and assay steps, a set of imaging and assay data points are generated.

Figure 28:
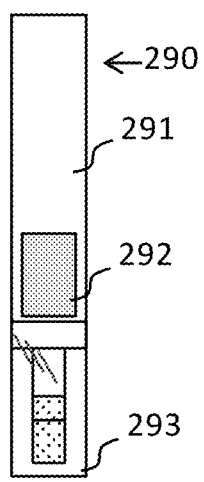
FIG. 28 is a diagrammatic front view of a first embodiment of an automatable assay/collection device.
Figure 29:
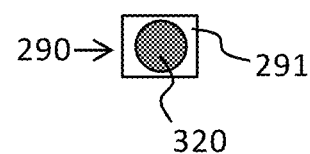
FIG. 29 is a diagrammatic top view of the FIG. 28 assay/collection device.
Figure 31:
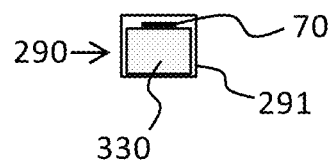
FIG. 31 is a diagrammatic bottom view of the FIG. 30 uncapped assay/collection device.
Figure 30:
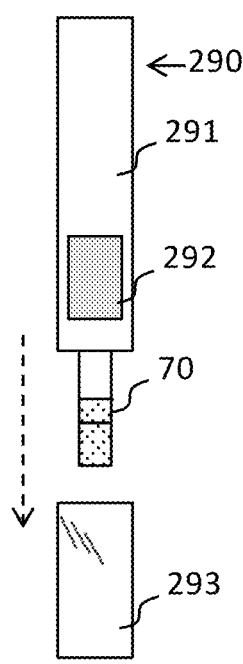
FIG. 30 is the FIG. 28 assay/collection device with the cap removed, leaving an uncapped assay/collection device.
Figure 32:
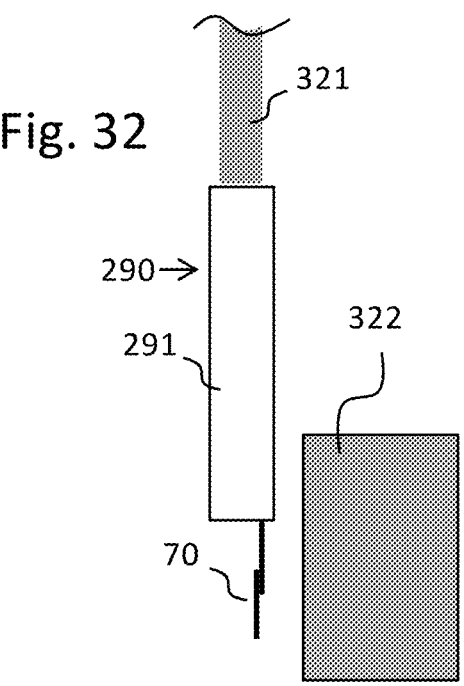
FIG. 32 is a diagrammatic side view of the FIG. 30 uncapped assay/collection device on an automated workstation.

A key advantage to the strip-based assay collection device described in FIGS. 7-10 is that it can be further incorporated into more complex devices able to accommodate additional useful features including easier collection methods and the ability to automate some or all of the analysis steps. FIGS. 28-32 illustrate one embodiment of such a device. FIG. 28 is a diagrammatic front view of an assay/collection device 290 configured with the FIG. 7 device inserted into a cartridge 291 and covered with a cap 293. The cartridge has a location for an identifier label 292 that can be automatically scanned. With the cap on, the sample region becomes enclosed in an airtight housing. FIG. 29 is a diagrammatic top view of the FIG. 28 device showing a port 320 that can accommodate the probe of an automated workstation allowing the device to be moved around automatically. FIG. 30 is the FIG. 28 device with the cap in the process of being removed, thus exposing the sample region of the FIG. 7 device 70. FIG. 31 is a diagrammatic bottom view of the FIG. 28 device showing a desiccant 330 inside the cartridge. With the desiccant, the cap may be replaced immediately after collecting sample and the liquid sample will continue to dry in the airtight environment. FIG. 32 is a diagrammatic side view of the FIG. 28 device showing the device inserted onto the probe of an automated workstation 321. The device is shown after having been moved into a position where an imaging device 322 is able to record one or more images of the sample region and identifier label. After imaging, the probe is then able to move the device to a container where the extraction process can be performed.

FIG. 33 is a diagrammatic front view of an assay/collection device comprising a cartridge 341 and cap 343 similar to the FIG. 28 device, but also containing an additional connector piece 342 that attaches to the FIG. 7 device. The FIG. 33 device may be operated similar to the FIG. 28 device. In addition, the connector piece allows for a second option wherein the cap may serve as an extraction container by detaching from the cartridge. FIG. 34 shows the FIG. 34 device where the cartridge is in the process of being removed from the connector piece. FIG. 35 is a diagrammatic bottom view of the removed cartridge showing the desiccant 330 inside the cartridge.

Figure 36:
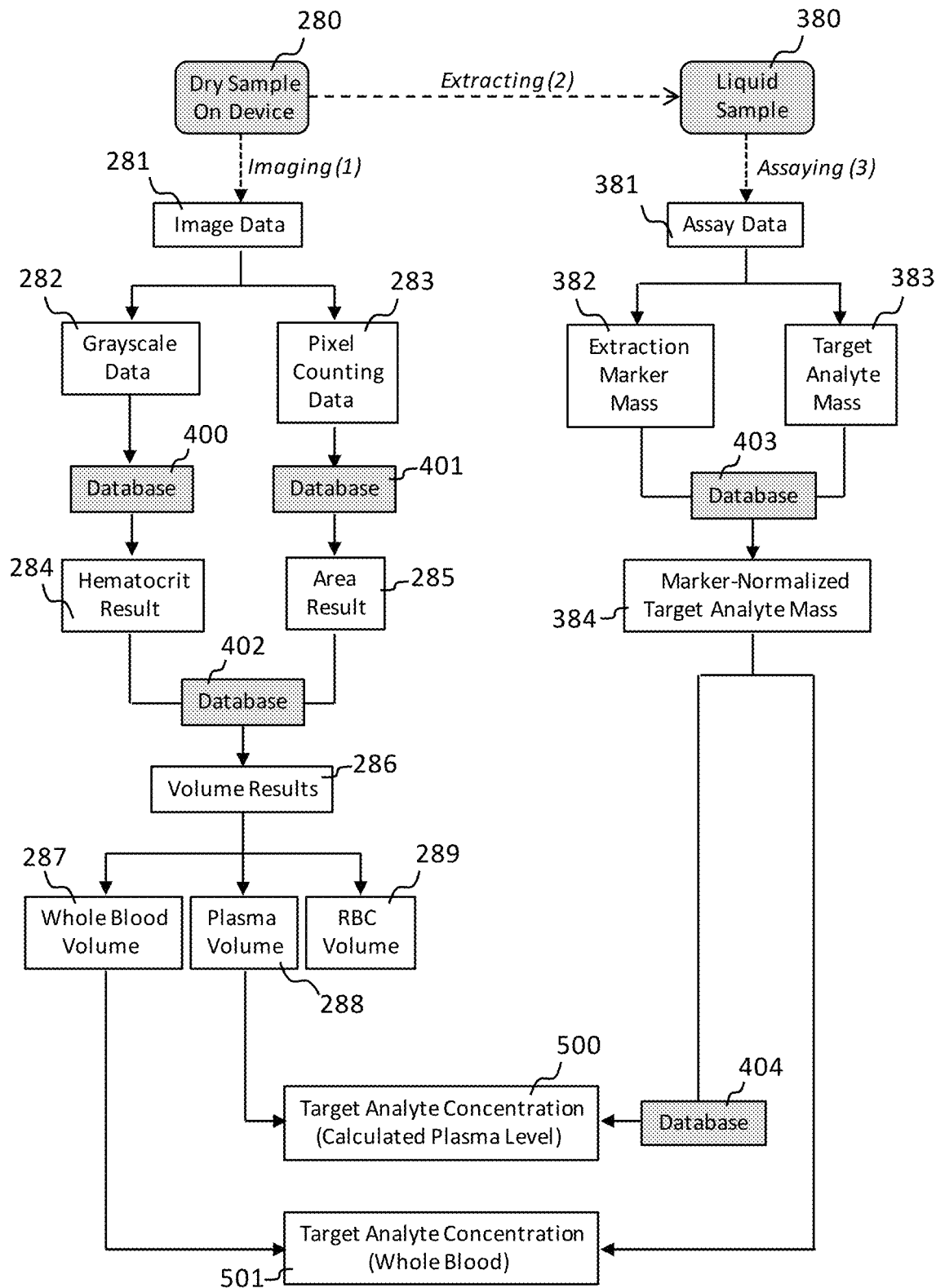
FIG. 36 is a flow chart describing step, elements and stages involved in the method of the invention.

FIG. 36 is a flowchart that outlines a sequence of steps and intermediate stages by which a dry sample on an assay/collection device produces one or more results. The dry sample on the device 280 first undergoes an imaging step to generate image data 281 then undergoes an extracting step to generate a liquid sample 380 which in turn undergoes an assaying step to generate assay data 381. The image data and assay data are then received by the computing device for analysis. The image data comprises grayscale data 282 which is analyzed with a database 400 to derive a hematocrit result 284 (the hematocrit value of the liquid blood sample that was dried onto the assay/collection device). The image data further comprises pixel counting data 283 which is analyzed with a database 401 to derive an area result 285. The hematocrit result and area result are then analyzed together in a database 402 to derive a volume result 286. Because the hematocrit result is known, the volume result can be further distinguished as the total whole blood volume 287 and the portion of that volume comprising the plasma volume 288 and red blood cell (RBC) volume 289. The assay data comprises both the target analyte mass 383 and the extraction marker mass 382 which are analyzed together in a database 403 to drive a marker-normalized target analyte mass 384. The marker-normalized target mass and whole blood volume can then be combined to derive a target analyte concentration 501. Alternately, or in addition, the marker-normalized target analyte mass can be analyzed in a database 404 to derive the fraction of the mass predicted to be in the plasma, and this value can be combined with the plasma volume to derive the target analyte concentration calculated to be in the plasma 500.

The various databases identified in the FIG. 36 flowchart are incorporated within the computing device and, typically, exist as tables of values, identifiers, calculations, etc. Each database is generated from the input of known values and is structured in a way to analyze or assist in the analysis of unknown values. For example, database 400 contains grayscale values from images of dried blood samples with known hematocrit levels, database 401 contains pixel counts from images of dried blood samples with known volume levels, and database 402 contains data from dried blood samples where the volume, area and hematocrit are known for each sample. In some embodiments, databases 400, 401 and 402 may be considered a single database.

Figure 37A:
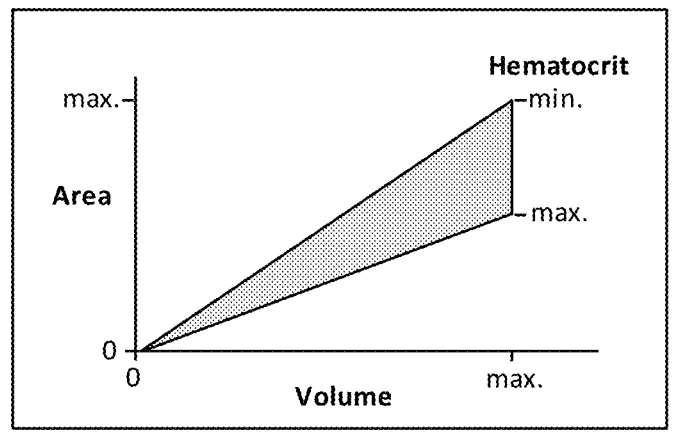
FIG. 37A is a graph depicting the data in a database that relates area, hematocrit and volume measurements of a dried blood sample on an assay/collection device.
Figure 37B:
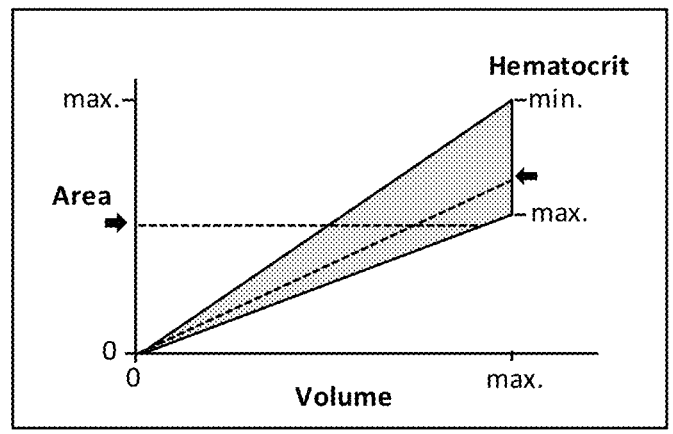
FIG. 37B is another graph depicting the data in a database that relates area, hematocrit and volume measurements of a dried blood sample on an assay/collection device.
Figure 37C:
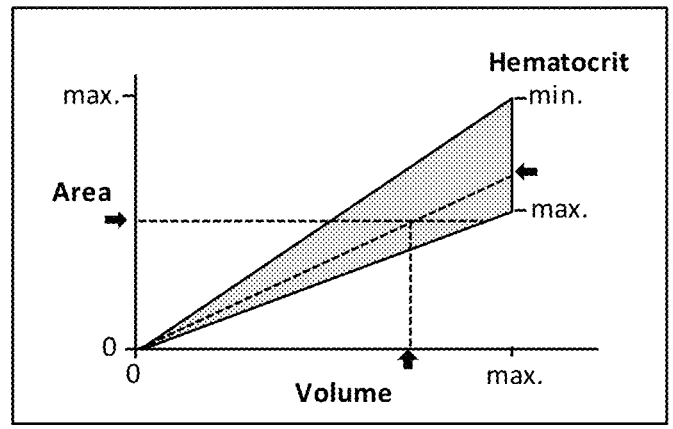
FIG. 37C is another graph depicting the data in a database that relates area, hematocrit and volume measurements of a dried blood sample on an assay/collection device.

In some cases, the functioning of the databases can be better understood through graphical representation. FIGS. 37A-37C are a series of diagrams that graphically illustrates the relationship between the hematocrit, area and volume values of a dried sample on an assay/collection device (the relationship analyzed in database 402). For each property a range is established reflecting the minimum and maximum value that can be analyzed (for example the volume range for a spot-based assay/collection device may be 0-50 µl). The shaded region shown in FIG. 37A indicates the measurable range of the system, wherein the input of any two variables will determine the third. FIG. 37B shows a set of dotted lines corresponding to a hematocrit measurement (received from database 400) and an area measurement (received from database 401). As shown in FIG. 37C, the point where the two dotted lines intersect defines the volume of the sample.

Figure 38:
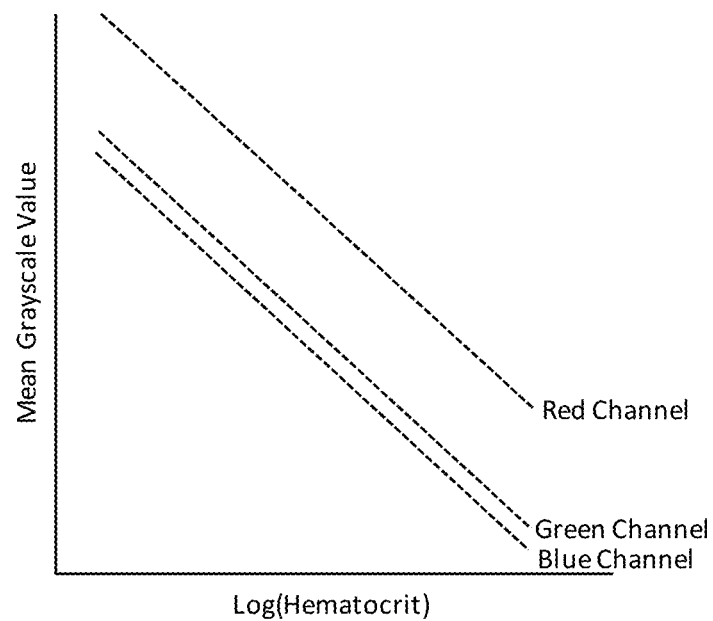
FIG. 38 is a graph illustrating the data in a database that correlates the change in grayscale values as a function of sample hematocrit for multiple dried blood samples on an assay/collection device measured at a single time point.
Figure 39:
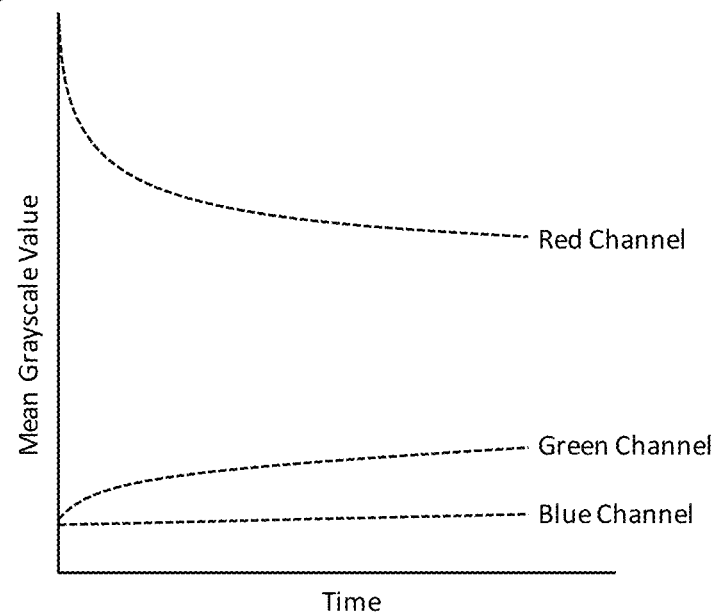
FIG. 39 is a graph illustrating the data in a database that correlates the change in grayscale values as a function of time for a single dried blood sample on an assay/collection device.

FIG. 38 graphically illustrates the relationship between the mean grayscale values (for all three color channels of an imaging device) and hematocrit values of a dried sample on an assay/collection device (the relationship analyzed in database 400). The graph represents a single time point and shows a linear, inverse correlation between the mean grayscale and hematocrit levels. On its own, this relationship would suggest that any of the three channels alone would be suitable for defining the hematocrit value. However, dried blood samples undergo continuous biochemical changes over time and this change affects the mean grayscale value (the changes are related to the conversion of hemoglobin molecules to methemaglobin and hemichrome). FIG. 39 graphically illustrates the relationship between the mean grayscale value (for all three color channels of an imaging device) and the hematocrit value of a single dried sample on an assay collection device taken at multiple time points (over a period of approximately 30 days). The graph shows a dramatic early shift in the red channel to darker grayscales and a smaller shift in the green channel to lighter grayscale values. In contrast, the blue channel shows very little shift during this period (this transition can be visually observed on a dried blood spot as the shifting from a reddish to brownish hue over time). If the numbers for the three color channels are regarded collectively as a single "RGB value", then database 400 can be described as having a set of hematocrit values with each value corresponding to multiple RGB values. It is important to note that the operative principal of the database is that each RGB value (within acceptable standard deviation) corresponds to a single hematocrit value. This principal thus allows the computing device to measure an unknown sample, define an RGB value for that sample, and search the database to identify the single hematocrit value associated with that RGB value.

Figure 40:
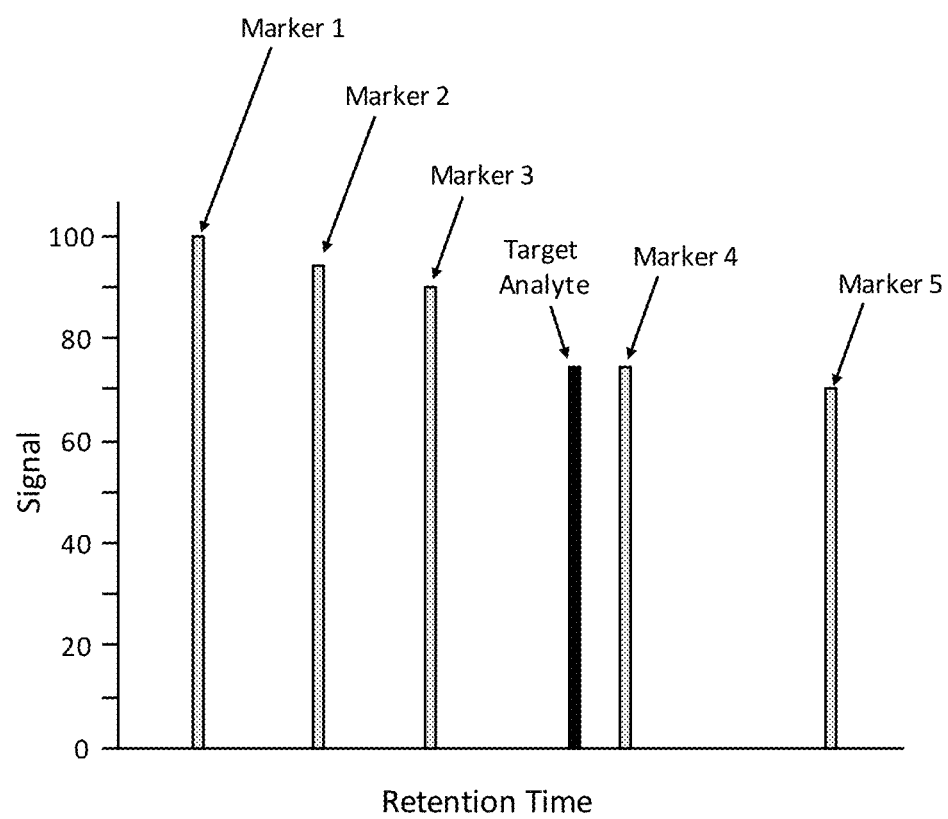
FIG. 40 is a graph illustrating the data in a database that correlates the extraction efficiency of a target analyte relative to the extraction efficiency of multiple extraction markers contained on an assay/collection device.

In a preferred embodiment, database 403 in the FIG. 36 flowchart contains a list of extraction marker analytes and target analytes along with values describing the relative extraction efficiencies of each analyte under various conditions. Data for this database can be gathered by drying multiple analytes together on a device at known levels, extracting the analytes under a defined set of conditions, and comparing the amount of each analyte co-extracted. FIG. 40 is a graph comparing the signals of a target analyte and 5 markers dried onto an assay/collection device at known levels. With a sufficient number of such datasets, the computing device can calculate extraction efficiency when the target analyte is analyzed in an unknown sample.

In some embodiments, assay/collection devices incorporating extraction markers may be used to analyze target analytes in non-blood samples such as urine and saliva.

A set of examples related to various parts of the invention are provided below:

Example 1: Assay/Collection Devices

Assay/collection devices were produced using Whatman DMPK-C paper as the absorbent material. For the strip-based devices similar to the design described in FIG. 3, the paper was first cut into a 6×30 cm sheet and a fill line was drawn 5 mm in from one of the 30 cm edges. This new sheet was then cut into strips of three different widths (4, 5 and 6 mm). Multi-strip devices similar to the configuration described in FIG. 17 were produced by affixing these strips to a cardboard backing with double-sided tape, allowing for the fill line end of the strip to overhang the backing by 1.5 cm.

For the strip-based devices similar to the design described in FIG. 7 the DMPK-C paper was first cut into an 8×300 mm sheet. A transparent sheet of plastic was then cut to a dimension of 5×30 cm and a fill line was drawn onto one of the 30 cm edges. This side of the plastic sheet was then attached to the DMPK-C paper with double-sided tape by applying a 3×300 mm strip of tape along the side of the plastic sheet and overlapping the paper sheet 3 mm along one of its long sides, leaving 5 mm of paper extending out. This new sheet was then cut into strips of three different widths (4, 5 and 6 mm). For the production of multi-strip devices similar to the design shown in FIG. 12, a cardboard backing was made with pockets suitable for fitting the plastic support of the strip, and the strip was slid into these pockets with the sample region extending out.

For the spot-based devices similar to the design described in FIG. 13, the DMPK-C paper was first cut into rectangles 3×8 cm in dimension and affixed to a cardboard frame with double-sided tape. Circles were then drawn onto the paper 10 mm in diameter. For some studies, Whatman FTA DMPK-C collection cards were used as the starting component for the spot-based device.

Example 2: Imaging Devices

Imaging devices, similar to the device described in FIG. 20, were produced using two models of Epson flatbed scanners (the Perfection V370 and the Perfection V550). An insert similar to the one described in FIGS. 20-22 was produced using a cardboard stock material cut to dimensions suitable for fitting over the plate of the flatbed scanners. A calibration target was created by excising the numerically labeled gray scale image from a Wolf-Faust IT8.7/2 color calibration target and affixing the excised portion of the tile to the bottom side of the insert.

Example 3: Preparation of Capillary and Venous Blood Samples with Defined Hematocrits Capillary and venous whole blood was collected and adjusted to defined hematocrit values. These samples were then used to generate calibration data and to test out the system as control material. For capillary samples, human whole blood was collected via finger prick into anticoagulant-containing tubes and pooled into a single tube. A portion of this blood was then spun down in a microcentrifuge tube and the plasma was removed and saved for diluting whole blood samples. The remaining whole blood was analyzed for hematocrit value and aliquoted into glass Durham tubes at various volumes calculated to provide a desired packed red blood cell volume into each tube. The tubes were then spun down in a microcentrifuge to create packed red blood cells. The packed red blood cell volume was measured for each tube and plasma was then added or removed to obtain a desired hematocrit value for each tube. For venous samples, human whole blood was collected via venous draw into tubes containing anticoagulant. A single tube of blood was then used to create samples with different hematocrit values using the method described with the capillary blood samples.

Example 4: Collection of Dried Blood Samples

The blood samples described in Example 3 were collected onto the assay/collection devices described in Example 1 and allowed to dry under various conditions of time, temperature and humidity. In most cases, the blood was collected at defined volumes.

For the spot-based collection devices, blood was collected by gently inverting the sample tube until the red blood cells were homogeneously suspended in the plasma then quickly dispensing a spot onto the device with a pipettor. Volumes collected onto the devices typically ranged from 10-40 µl.

For the strip-based collection devices, blood was collected by gently inverting the sample tube until the red blood cells were homogeneously suspended in the plasma then quickly dispensing a defined volume of blood onto a hydrophobic surface with a pipettor, forming a bead of blood. While continuing to work quickly, the sample region of a strip-based collection device was placed in contact with the bead and the sample was allowed to migrate onto the sample region. Volumes collected onto the devices typically ranged from 8-16 µl.

An alternate approach was also used for collecting blood onto the strip-based assay collection devices, wherein the bead of blood was dispensed onto a hydrophobic sheet of weighing paper placed on an analytical balance. The weight was then recorded before and after collection of the bead onto the device, thus allowing for a certain amount of residual sample to remain on the weighing paper.

In some cases, the blood sample was at room temperature prior to collection, while other times the blood was first warmed to 37° C. just before collection.

Example 5: Imaging of Dried Blood Samples

After allowing sufficient time for the blood sample to dry on the collection device, the dried-sample-containing collection device was imaged on one of the imaging devices described in Example 2. These images were then saved on a computer in standard imaging files for analysis.

Example 6: Analysis of Image Data for Area Determination of a Dried Sample

The digital imaging data from dried blood samples collected and imaged as described in Examples 4 and 5, respectively, was subsequently analyzed for various attributes. One of these attributes is the area encompassing the sample portion of the image. This is determined by summing up the number of pixels comprising the sample portion of the image and dividing this number by an area/pixel value (defined by the instrument or determined with a known area reference on the image).

Figure 41:
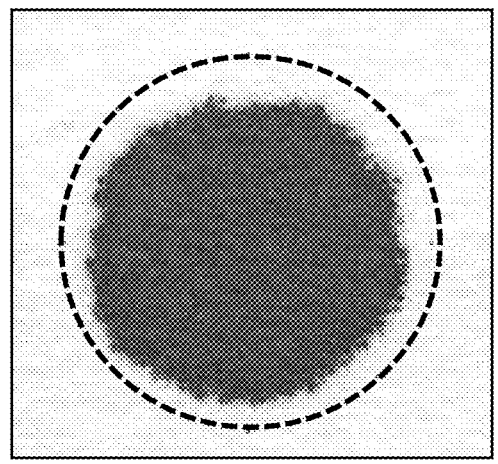
FIG. 41 is a digital image of a dried blood spot on a spot-based assay/collection device.
Figure 42:
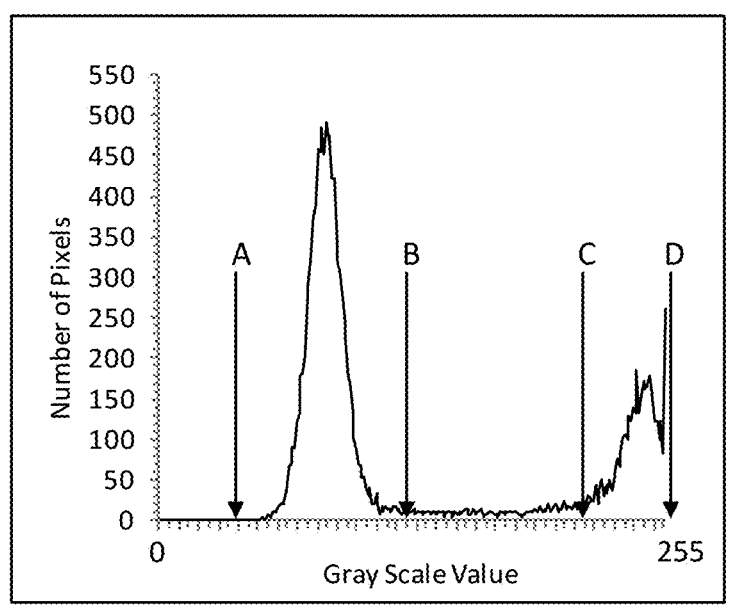
FIG. 42 is a histogram showing the total number and (blue channel) grayscale distribution of pixels within the dotted circle superimposed on the digital image in FIG. 41.

FIG. 41 shows the digital image of a dried blood sample collected on a spot-based assay/collection device. The image is a grayscale recording from the blue channel of the imaging device. A circle superimposes the sample spot encompassing every pixel that comprises the sample along with certain number of pixels outside the sample. FIG. 42 shows a histogram of the FIG. 41 image, showing the total number and grayscale distribution of pixels inside the superimposed circle. The histogram is separated into three sections. The section between arrows A and B encompass the fully (sample) saturated pixels defining the sample spot, as pixels measured clearly inside the spot remain in this section. The section between arrows C and D encompass pixels fully unsaturated, as pixels measured clearly outside the sample spot remain in this section. The section between arrows B and C encompass partially saturated pixels which reside predominantly around the border or perimeter of the spot, and are indicative of areas on the paper that are not fully saturated with blood sample.

In summing up the number of pixels comprising the area of the sample spot, multiple methods may be used. One method is to sum up only the saturated pixels. Another method is to sum up both the saturated and unsaturated pixels and give both types equal weight. Still another method is to sum up both saturated and unsaturated pixels but give them different weights. The weighting of the pixels could be performed through a variety of methods including, but not limited to, supervised machine learning methods using a sufficient number of training examples. Data related to these determinations would be typical of the information located in the database 401 of the FIG. 36 flowchart.

Figure 43:
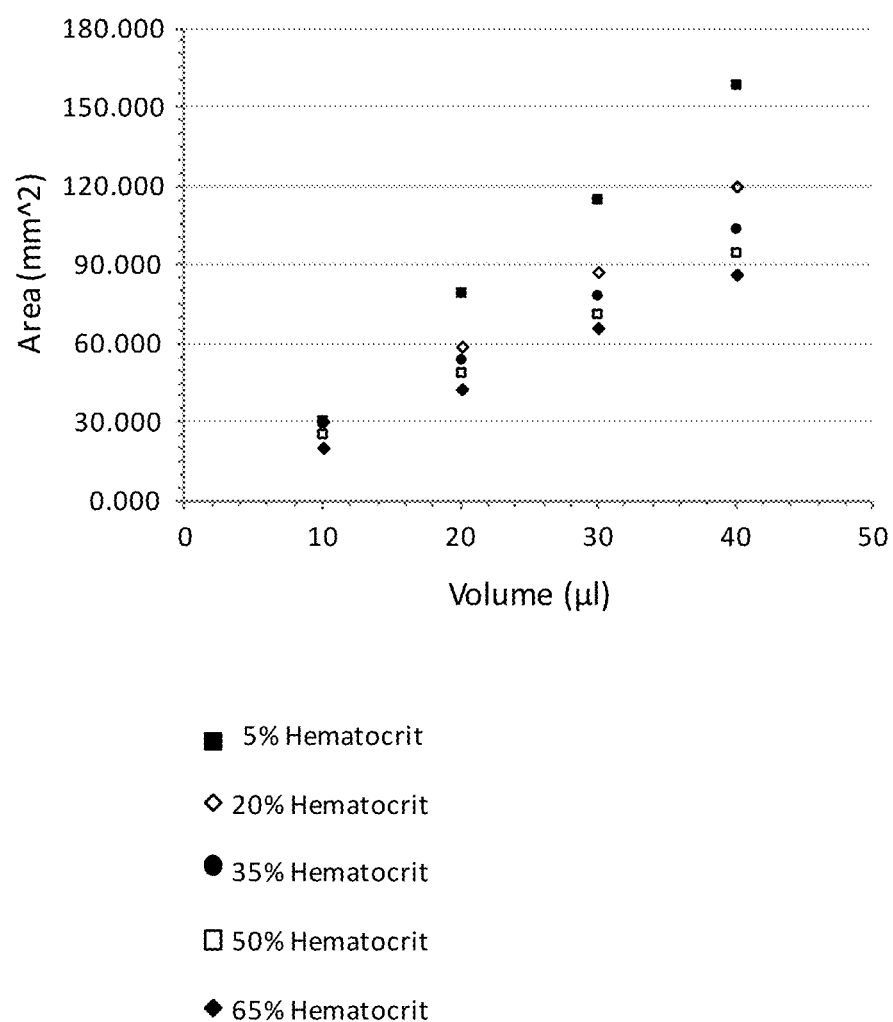
FIG. 43 is a graph plotting the area of a dried blood spot as a function of the applied volume for a set of blood samples with hematocrit levels ranging from 5%-65%.

FIG. 43 is a graph plotting the area of a dried blood sample (such as the one shown in FIG. 41) as a function of the applied volume for a set of blood samples with hematocrit levels ranging from 5-65%. For example, a 30 µl sample with a 50% hematocrit (open squares) was found to have an area of 70.7 mm^2.

The graph presented in FIG. 43 allows for two types of interpolation. One interpolation allows for the calculation of area based on the volume of a sample with a known hematocrit. Another interpolation allows for the calculation of area based on the hematocrit of a sample with a known volume. Taken together, it becomes possible to interpolate any hypothetical data point between the volume range (10-40 µl), hematocrit range (5-65%) and area range (20.4-157.9 mm^2), such that given any two parameters, the third can be interpolated. This relationship provides the basis for the database 402 of the FIG. 36 flowchart.

Example 7: Analysis of Image Data for Hematocrit Determination

Figure 44A:
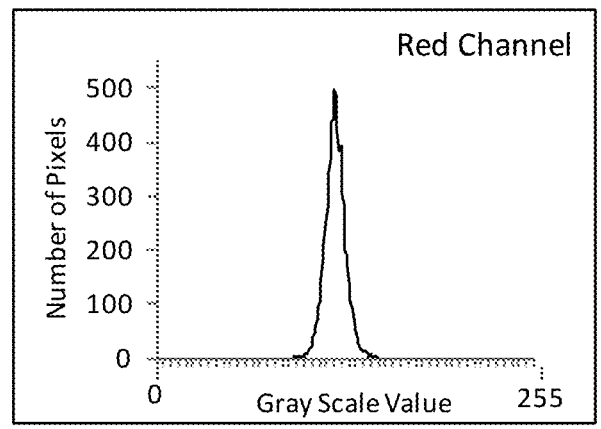
FIG. 44A is a histogram generated from the digital image of a single dried blood sample, showing the total number and grayscale distribution of pixels for each of the three color channels.
Figure 44B:
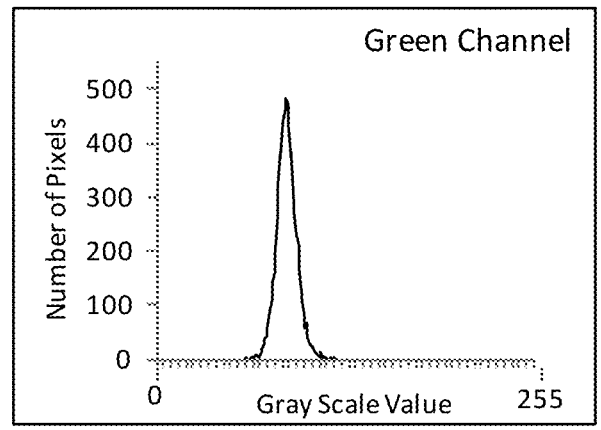
FIG. 44B is another histogram generated from the digital image of a single dried blood sample, showing the total number and grayscale distribution of pixels for each of the three color channels.
Figure 44C:
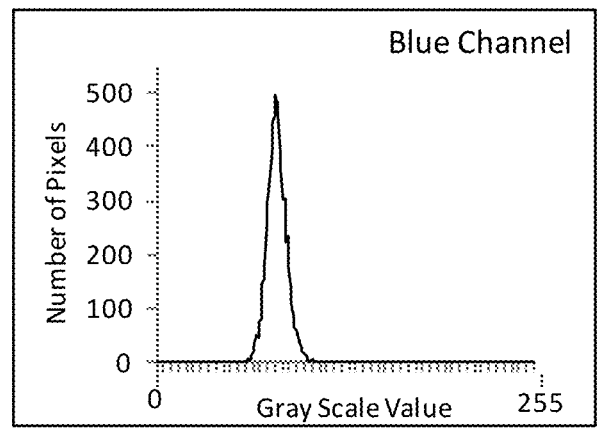
FIG. 44C is another histogram generated from the digital image of a single dried blood sample, showing the total number and grayscale distribution of pixels for each of the three color channels.

The present invention makes use of the surprising finding that the grayscale values obtained from a dried blood sample comprise a dataset indicative of the hematocrit value associated with that sample. These datasets can be stored in a database and used to determine the hematocrit value associated with an unknown sample. This relationship provides the basis for the database 400 shown in the FIG. 36 flowchart. FIGS. 44A-44C show a set of histograms, FIGS. 44A, 44B, and 44C, that provide an example of the type of datasets that may be stored in the database. Each histogram shows the number and grayscale distribution of pixels, taken from the saturated portion of a dried blood sample image, derived from each of the three color channels used by the imaging instrument.

A simple way to express such a dataset is to determine the mean value for all of the pixels in a given histogram which, in the case of this example, is 121.902 for the red channel, 88.325 for the green channel and 81.793 for the blue channel. The sample could thus be considered to have an "RGB value" of 121.902/88.325/81.793. The blood sample used to generate this dataset had a hematocrit value of 50% (prepared from capillary blood as described in example 3). Thus, this correlation can be stored in a database as 121.902/88.325/81.793=50.

Figure 45:
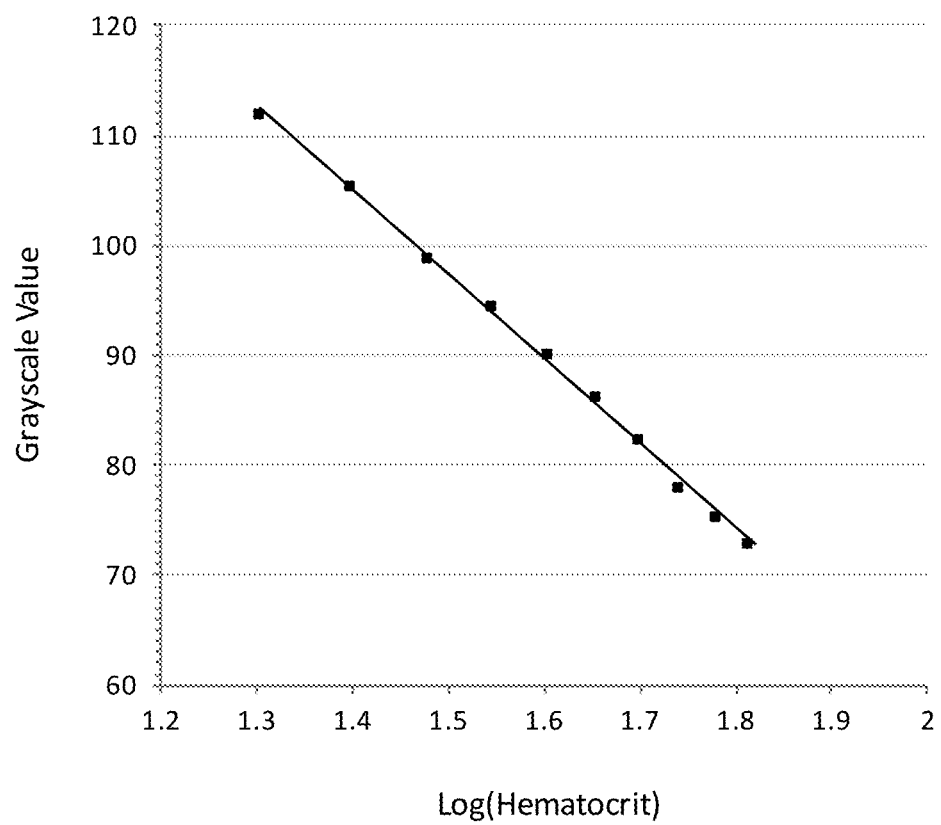
FIG. 45 is a graph showing the (blue channel) grayscale values of dried blood samples on an assay/collection device plotted as a function of hematocrit level.

FIG. 45 is a graph showing the mean grayscale values (from the blue channel) for dried blood samples plotted as a function of log hematocrit using a hematocrit range of 20-65%. This data shows a clear, linear dose response within this range, indicating the feasibility of this colorimetric signal for distinguishing different hematocrit values in dried blood samples.

Example 8: Calibration of Grayscale Values with a Standardized Reference

Figure 46:
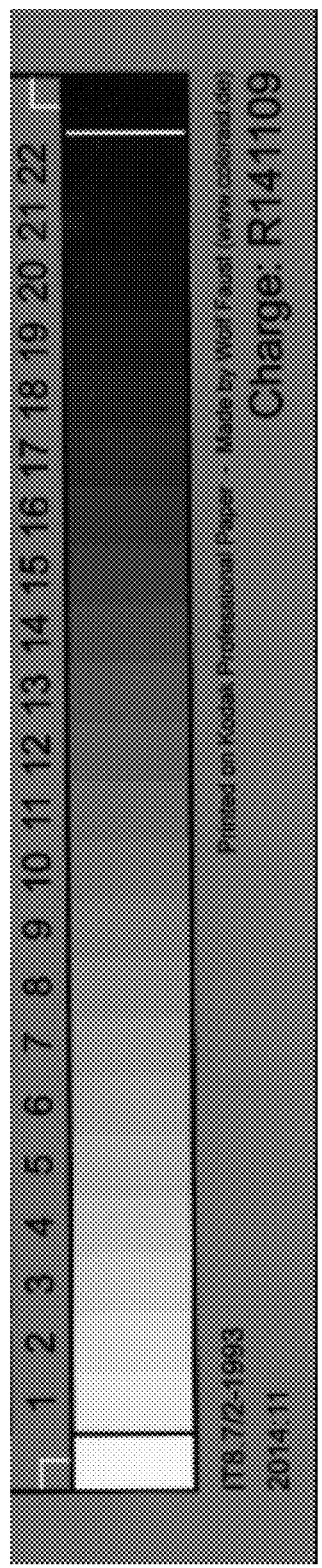
FIG. 46 is a numerical grayscale chart excised from a Wolf-Faust IT8.7/2 color calibration target.
Figure 47A:
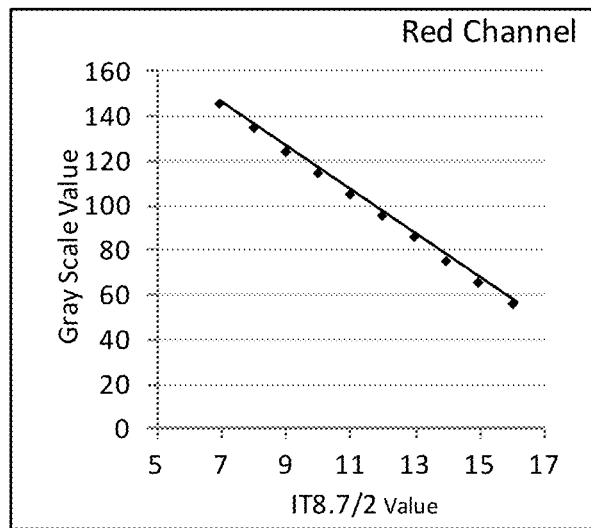
FIG. 47A is a calibration curve used to convert grayscale values into values specific to a IT8.7/2 calibration chart that is imaged alongside the assay/collection devices.
Figure 47B:
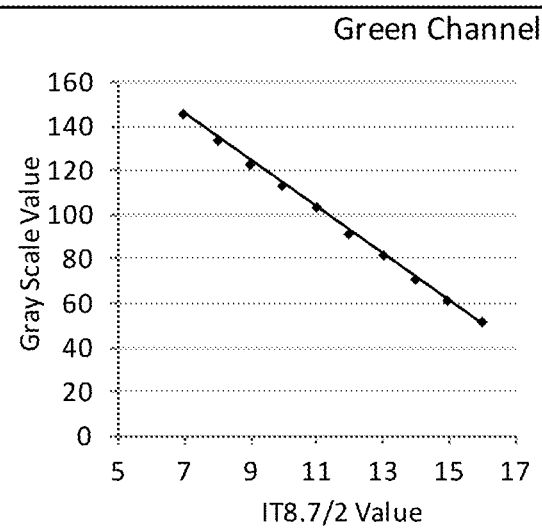
FIG. 47B is another calibration curve used to convert grayscale values into values specific to a IT8.7/2 calibration chart that is imaged alongside the assay/collection devices.
Figure 47C:
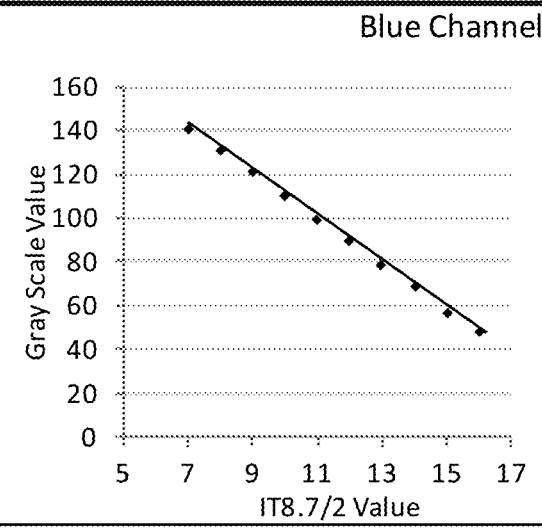
FIG. 47C is another calibration curve used to convert grayscale values into values specific to a IT8.7/2 calibration chart that is imaged alongside the assay/collection devices.

On any imaging device, grayscale values may fluctuate slightly for a given image from scan-to-scan. If this fluctuation is not accounted for, accuracy and precision may be reduced, particularly when calculations use stored calibration data. To address scan-to-scan fluctuations, a color calibration target, such as the calibration target 201 attached to the insert described in FIG. 22, may be incorporated with every scan to provide continuous recalibration of the image. As noted in Example 2, an imaging instrument was constructed that incorporates a numerical grayscale chart excised from a Wolf-Faust IT8.7/2 color calibration target. A reproduction of this chart is shown in FIG. 46. The chart contains 22 individual, standardized grayscale cells and associates each cell with a number. Using this target, a set of three calibration curves (one for each channel) can be obtained on every scan, translating the mean grayscale value into a mean "IT8.7/2" value. FIGS. 47A, 47B, and 47C provide an example of a set of these calibration curves.

Figure 48:
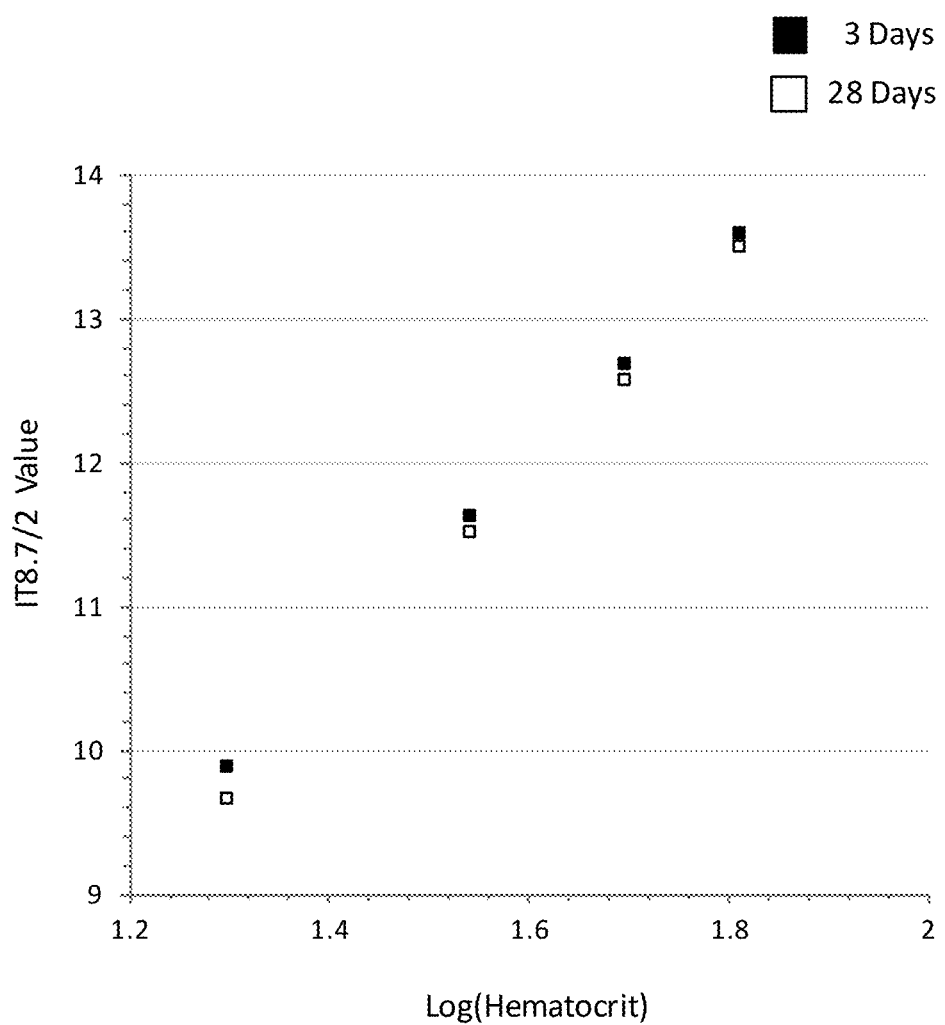
FIG. 48 is a graph plotting blue channel color signal from dried blood samples as a function of hematocrit level, comparing the results of images obtained 3 days and 28 days after sample collection onto assay/collection devices.

Using this calibration method, FIG. 48 shows a graph of the blue channel IT8.7/2 values plotted as a function of log(hematocrit) for dried blood samples prepared from four different hematocrit levels (20%, 35%, 50% and 65%). The samples were scanned at 3 days (black squares) and 28 days (white squares) after collection onto assay/collection devices.

A study similar to the one described in FIG. 48 was performed on a larger scale at three different hematocrit levels (25%, 45% and 65%) with sixteen dried blood samples prepared for each level. Table 1 below shows the IT8.7/2 values for each of the three color channels. This data indicates very good precision from sample-to-sample and demonstrates the kind of data that may be stored in the database 400 of the FIG. 36 flowchart.

TABLE 1

| | 65% Hematocrit | | | | 45% Hematocrit | | | | 25% Hematocrit | | |
|---|---|---|---|---|---|---|---|---|---|---|---|
| REP. | RED | GREEN | BLUE | REP. | RED | GREEN | BLUE | REP. | RED | GREEN | BLUE |
| 1 | 10.171 | 13.545 | 13.591 | 1 | 8.426 | 12.420 | 12.559 | 1 | 5.893 | 10.311 | 10.773 |
| 2 | 10.236 | 13.663 | 13.743 | 2 | 8.388 | 12.503 | 12.643 | 2 | 5.925 | 10.298 | 10.789 |
| 3 | 10.166 | 13.520 | 13.582 | 3 | 8.611 | 12.639 | 12.777 | 3 | 5.834 | 10.223 | 10.764 |
| 4 | 10.079 | 13.512 | 13.549 | 4 | 8.482 | 12.524 | 12.644 | 4 | 5.980 | 10.306 | 10.800 |
| 5 | 9.775 | 13.319 | 13.431 | 5 | 8.728 | 12.586 | 12.740 | 5 | 5.881 | 10.228 | 10.688 |
| 6 | 9.818 | 13.359 | 13.483 | 6 | 8.787 | 12.609 | 12.767 | 6 | 5.781 | 10.188 | 10.699 |
| 7 | 9.688 | 13.353 | 13.476 | 7 | 8.368 | 12.429 | 12.561 | 7 | 5.852 | 10.227 | 10.758 |
| 8 | 9.887 | 13.440 | 13.498 | 8 | 8.503 | 12.499 | 12.651 | 8 | 5.893 | 10.289 | 10.812 |
| 9 | 9.875 | 13.360 | 13.496 | 9 | 8.530 | 12.575 | 12.725 | 9 | 5.524 | 10.331 | 10.346 |
| 10 | 9.878 | 13.398 | 13.524 | 10 | 8.447 | 12.543 | 12.672 | 10 | 5.630 | 10.191 | 10.477 |
| 11 | 10.023 | 13.554 | 13.679 | 11 | 8.646 | 12.562 | 12.677 | 11 | 5.796 | 10.226 | 10.662 |
| 12 | 9.980 | 13.533 | 13.590 | 12 | 8.660 | 12.618 | 12.765 | 12 | 5.876 | 10.274 | 10.688 |
| 13 | 9.814 | 13.421 | 13.439 | 13 | 8.357 | 12.460 | 12.600 | 13 | 5.874 | 10.505 | 10.756 |
| 14 | 9.932 | 13.483 | 13.528 | 14 | 8.575 | 12.585 | 12.699 | 14 | 5.810 | 10.591 | 10.626 |
| 15 | 9.769 | 13.428 | 13.527 | 15 | 8.585 | 12.555 | 12.686 | 15 | 5.807 | 10.471 | 10.711 |
| 16 | 9.781 | 13.382 | 13.494 | 16 | 8.284 | 12.404 | 12.521 | 16 | 5.901 | 10.401 | 10.744 |

Example 9: Effect of Extraction Markers on Accuracy

Figure 49A:
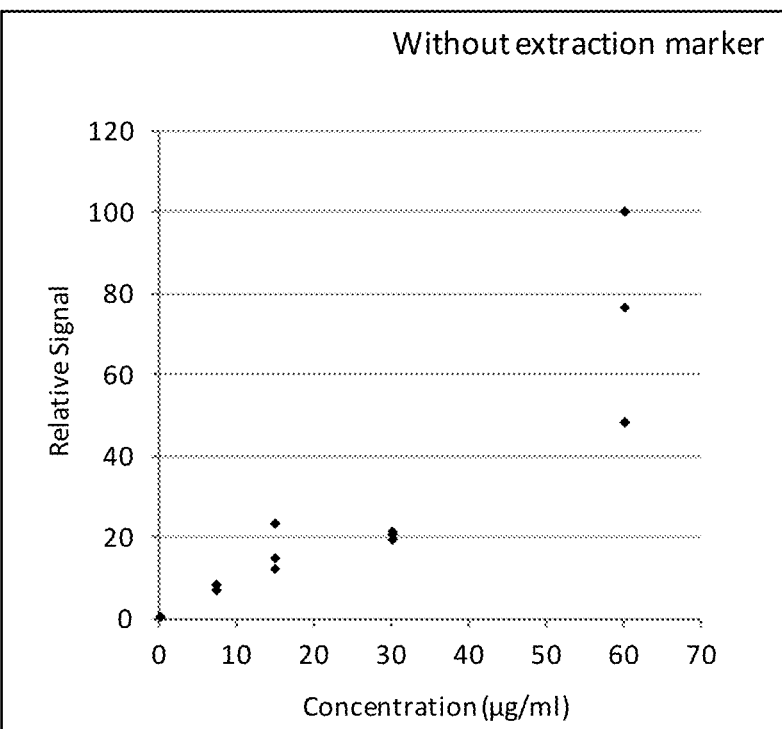
FIG. 49A is a graph comparing the dose response of phenobarbital extracted from dried blood samples collected on assay/collection devices, where the relative signal was plotted without (A) and with (B) extraction marker normalization.
Figure 49B:
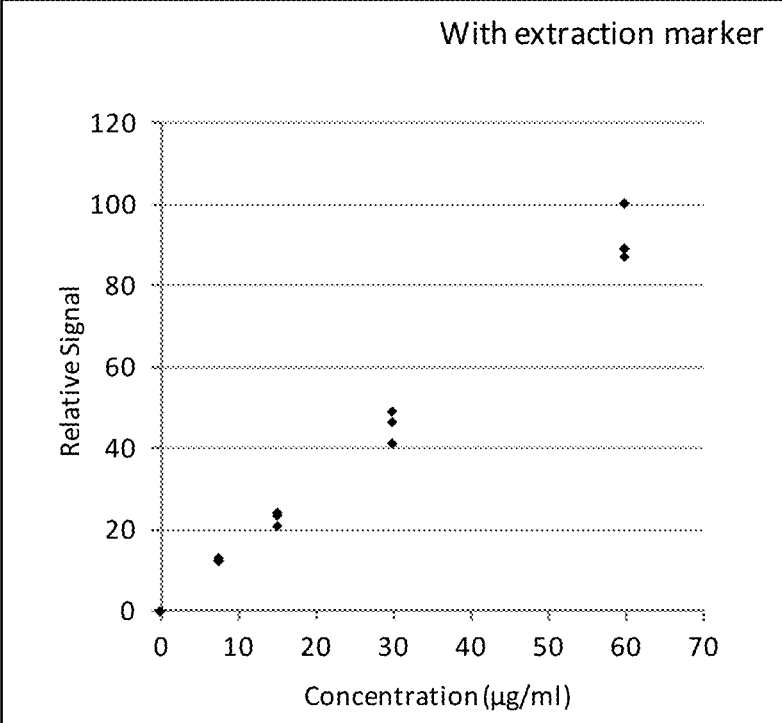
FIG. 49B is another graph comparing the dose response of phenobarbital extracted from dried blood samples collected on assay/collection devices, where the relative signal was plotted without (A) and with (B) extraction marker normalization.

To demonstrate the effect of incorporating dried extraction markers onto the assay/collection devices, a study was performed using phenobarbital as an analyte and deuterated phenobarbital (D-Phenobarbital) as an extraction marker. Deuterated phenobarbital was coated onto a set of strip-based assay/collection devices (6 mm width strips prepared as described in Example 1) to obtain 300 nanograms of D-phenobarbital coated and dried onto the sample region. Blood samples were prepared by spiking phenobarbital into five separate aliquots of blood to obtain final concentrations of 0, 7.5, 15, 30 and 60 µg/ml phenobarbital. 12 µl of sample was collected and dried overnight onto the strip, with each level being performed in triplicate. The following day all samples were extracted with 400 µl water and 15 minutes of slow shaking (an extraction process designed to be sub-optimal) spiked with a post-extraction internal standard, centrifuged and analyzed on an Agilent 6460 LC/MS system. FIG. 48 shows the results of the study, comparing relative signal for results not normalized (FIG. 49A) and normalized (FIG. 49B) to the D-phenobarbital extraction marker. These results indicate that the extraction marker can correct for significant variability that may occur in the extraction step.

What is claimed is:

1. A method for determining the volume of a blood sample, the fraction of the blood sample volume composed of plasma, and the fraction of the blood sample volume composed of red blood cells, the method comprising:
   a) collecting the blood sample on a collection device, the collection device comprising an absorbent material capable of collecting the blood sample by capillary action and producing an observable colorimetric pattern from the blood sample, wherein the absorbent material incorporated in the collection device comprises a strip with a fill line such that, when the blood sample is collected on the collection device, the strip is contacted with the blood sample for a period of time sufficient for the blood sample to migrate to the fill line;
   b) drying the blood sample on the collection device;
   c) recording the colorimetric pattern on the collection device as a first set of data points with an imaging device;
   d) receiving the first set of data points from the imaging device with a computing device operatively connected to the imaging device using an executable software program, wherein the first set of data points comprises grayscale values and pixel counts;
   e) determining a hematocrit value of the blood sample collected by the collection device by comparing the grayscale values to a first database of grayscale values of images of blood samples with known hematocrit values;
   f) determining an area value of the blood sample collected by the collection device by comparing the pixel counts to a second database of pixel counts of images of blood samples with known volumes;
   g) determining the volume of the blood sample collected by the collection device by comparing the hematocrit value and the area value to a third database of images of blood samples with known volumes, area values, and hematocrit values; and
   h) determining the fraction of the blood sample volume composed of plasma, and the fraction of the blood sample volume composed of red blood cells by comparing the the hematocrit value with the volume of the blood sample collected by the collection device.

2. The method of claim 1, wherein the absorbent material incorporated into the collection device comprises cellulose-based paper.

3. The method of claim 1, wherein the imaging device comprises a digital camera.

4. The method of claim 1, wherein the collection device with the dried blood sample can be transported without cold storage.

5. The method of claim 1, wherein the collection device with the dried blood sample can be transported without expedited delivery.

6. The method of claim 1, wherein the step of collecting the blood sample on the collection device is performed at a first location, and the collection device with the dried blood sample is transported without cold storage to a second location for the remaining steps.

7. A method for determining the concentration of a target analyte in a blood sample, the method comprising:
   a) collecting the blood sample on a collection device, the collection device comprising an absorbent material capable of collecting the blood sample by capillary action and producing an observable colorimetric pattern from the blood sample;

b) drying the blood sample on the collection device;

c) recording the colorimetric pattern on the collection device as a first set of data points with an imaging device;

d) receiving the first set of data points from the imaging device with a computing device operatively connected to the imaging device using an executable software program, wherein the first set of data points comprises grayscale values and pixel counts;

e) determining a hematocrit value of the blood sample collected by the collection device by comparing the grayscale values to a first database of grayscale values of images of blood samples with known hematocrit values;

f) determining an area value of the blood sample collected by the collection device by comparing the pixel counts to a second database of pixel counts of images of blood samples with known volumes;

g) determining the volume of the blood sample collected by the collection device by comparing the hematocrit value and the area value to a third database of images of blood samples with known volumes, area values, and hematocrit values; and h) determining the fraction of the blood sample volume composed of plasma, and the fraction of the blood sample volume composed of red blood cells by comparing the the hematocrit value with the volume of the blood sample collected by the collection device;

i) extracting the dried blood sample from the collection device with an extraction solution to produce a fluid sample extract;

j) determining the mass of the target analyte in the fluid sample extract with an assay; and k) combining the target analyte mass determination in step j) with the blood sample volume determination in step g) to derive the concentration of the target analyte in the blood sample.

8. The method of claim 7, wherein the absorbent material incorporated into the collection device comprises cellulose-based paper.

9. The method of claim 7, wherein the imaging device comprises a digital camera.

10. The method of claim 7, wherein the absorbent material incorporated in the collection device comprises a strip with a fill line such that, when the blood sample is collected on the collection device, the strip is contacted with the blood sample for a period of time sufficient for the blood sample to migrate to the fill line.

11. The method of claim 7, wherein the collection device with the dried blood sample can be transported without cold storage.

12. The method of claim 7, wherein the collection device with the dried blood sample can be transported without expedited delivery.

13. The method of claim 7, wherein the step of collecting the blood sample on the collection device is performed at a first location, and the collection device with the dried blood sample is transported without cold storage to a second location for the remaining steps.

14. The method of claim 7, wherein the assay incorporates techniques selected from the group consisting of: chromatography, mass spectrometry, immunoassays, chemical assays, biochemical assays, biological assays, and nucleic acid amplification assays.

15. The method of claim 7, wherein the collection device further comprises at least one extraction marker that is dried onto the absorbent material at known masses and is co-extracted with the target analyte to provide means for normalizing the sample blood volume concentration result.

16. The method of claim 7, wherein the software program further comprises a red blood cell partitioning coefficient database to derive the concentration of the target analyte in the plasma portion of the blood sample.

* * * * *